(12) United States Patent
Manoni et al.

(10) Patent No.: US 7,687,249 B2
(45) Date of Patent: Mar. 30, 2010

(54) POLYSACCHARIDE DERIVATIVES WITH HIGH ANTITHROMBOTIC ACTIVITY IN PLASMA

(75) Inventors: Marco Manoni, Milan (IT); Liana Salsini, Ripa (IT); Jacopo Chini, Florence (IT); Giovanni Cipolletti, Milan (IT)

(73) Assignee: Inalco S.p.A., Milan (IT)

( * ) Notice: Subject to any disclaimer, the term of this patent is extended or adjusted under 35 U.S.C. 154(b) by 256 days.

(21) Appl. No.: 10/557,584

(22) PCT Filed: Jul. 7, 2004

(86) PCT No.: PCT/EP2004/051391

§ 371 (c)(1),
(2), (4) Date: Nov. 15, 2005

(87) PCT Pub. No.: WO2005/014656

PCT Pub. Date: Feb. 17, 2005

(65) Prior Publication Data

US 2007/0042993 A1     Feb. 22, 2007

(30) Foreign Application Priority Data

Aug. 6, 2003 (IT) .......................... MI2003A1618

(51) Int. Cl.
*C12P 1/00* (2006.01)
*C12P 19/00* (2006.01)
*C12P 19/04* (2006.01)
*A01N 41/08* (2006.01)
*A61K 31/70* (2006.01)
*A61K 31/715* (2006.01)
*A61K 31/726* (2006.01)
*A61K 31/727* (2006.01)
*C07H 5/06* (2006.01)
*C07H 5/04* (2006.01)
*C08B 37/08* (2006.01)

(52) U.S. Cl. .......................... 435/101; 435/41; 435/72; 435/849; 514/23; 514/54; 514/56; 514/62; 536/20; 536/55.1; 536/55.2; 536/123

(58) Field of Classification Search .................. None
See application file for complete search history.

(56) References Cited

U.S. PATENT DOCUMENTS

| 5,550,116 | A | 8/1996 | Lormeau et al. |
| 5,958,899 | A | 9/1999 | Zoppetti et al. |
| 6,162,797 | A * | 12/2000 | Zoppetti et al. ............... 514/54 |
| 6,197,943 | B1 | 3/2001 | Casu et al. |
| 7,268,122 | B2 * | 9/2007 | Zoppetti et al. ............... 514/54 |
| 2003/0023079 | A1 | 1/2003 | Oreste et al. |

OTHER PUBLICATIONS

Li, et al.; characterization of the D-Glucuronyl C5-epimerase involved in the biosynthesis of Heparin and Heparan Sulfate; J. of Bio.Chem.; (2001); 20069-20077;vol. 276, No. 23.
Vann et al.; the structure of the capsular polysaccharide (K5) Antigen) of urinary-tract-infective *E.coli* O10:K5:H4; Eur.J.Biochem.; 116,359-364 (1981).
Casu et al.; heparin-like compounds prepared by chemical modification of capsular polysaccharide from *E.coli* K5*1; Carb.Res., 263:(2), 271-284 (1994).
Naggi et al; generation of anti-factor Xa active, 3-0-sulfated glucosamine-rich sequences by controlled desulfation of oversulfated heparins; Carb.Res.;336:(4), 283-290 (2001).

* cited by examiner

*Primary Examiner*—Christopher R Tate
*Assistant Examiner*—Aaron J Kosar
(74) *Attorney, Agent, or Firm*—Abelman, Frayne & Schwab

(57) ABSTRACT

The present invention relates to a process for the preparation of sulphated glycosaminoglycans derived from N— acetylheparosan which comprises: a) N-deacetylation and N-sulphation of the N-acetylheparosan polysaccharide prepared from natural or recombinant bacterial strain, preferably K5 *E. coli*, b) enzymatic epimerization with the glucuronyl C5-epimerase enzyme, c) partial O-sulphation followed by a partial O-desulphation, d) partial 6-O-sulphation, e) N-sulphation and an intermediate step of controlled depolimerization characterised by the fact that both O-sulphations (O-sulphation and 6O-sulphation) are partial.

Furthermore the invention relates to the products obtained according to the process which show a ratio between the anti-Xa activity and anti-IIa activity equal to or higher than 1 and to compositions comprising said products in combination with suitable and pharmaceutically acceptable excipients and/or diluent.

15 Claims, 18 Drawing Sheets

POLYSACCHARIDE DERIVATIVES WITH HIGH ANTITHROMBOTIC ACTIVITY IN PLASMA

FIELD OF THE INVENTION

The invention field is the preparation of sulphated polysaccharides with anticoagulant antithrombotic activity starting from polysaccharides with microbial origin.

PRIOR ART

Natural heparin is a polymer having glycosaminoglycanic structure, with variable molecular weights between 3,000 and 30,000 Da, made up of the sequence of repeated disaccharide units made up of uronic acid (L-iduronic or D-glucuronic) and of an amino sugar (glucosamine) bond to each other by β-1-4 bonds. Uronic acid can be sulphated in position 2 and glucosamine can be N-acetylated or N-sulphated and 6O-sulphated. Furthermore, glucosamine can also contain a sulphate group in position 3.

These substitutes are essential for the creation of the binding region with high affinity to antithrombin (ATIII) and to explicate the anticoagulant and antithrombotic activity of the polymer.

Heparin is the basic anticoagulant and antithrombotic agent for therapeutic use and, even up-to-date, is obtained by extraction from animal organs. In the attempt to substitute this supply source and, therefore, to satisfy the increasing material requests, eliminating at the same time any accidental contamination from infective agents, principally virus or prions, were developed in the last years, vary processes for the preparation of molecules with an heparin-like structure as well as alike characteristics, starting from N-acetyl heparosan polysaccharides having bacterial origin and, therefore, available without quantity limit.

The N-acetyl heparosan polysaccharide isolated from a few natural or recombinant K5 *Escherichia coli* or from *Pasteurella multocida* bacterial stocks, has the same basic structure of the natural heparin precursor made up of a repeated sequence of D-glucuronic acid and N-acetyl glucosamine bond to each other by α 1-4 bonds. The bond between the disaccharidic units is, on the contrary, β 1-4.

The uronic acid can be sulphated in two different positions and the glucosamine can be N-acetylated or N-sulphated and 6O-sulphated. Furthermore glucosamine can contain also a sulphate group in position 3.

The N-acetyl heparosan polysaccharide isolated from *E. coli* K5 (Vann W. F., Schmidt M. A., Jann B., Jann K. (1981) in Eur. J. Biochem 116, 359-364) was chemically modified as described by Lormeau et al. in U.S. Pat. No. 5,550,116 and by Casu et al (Carb. Res 263-1994-271-284) or chemically and enzymatically in the attempt to obtain products endowed with biological activity comparable to the one of extractive heparin.

Furthermore the semi synthetic products must undergo a depolymerization process to decrease molecular weight which makes the product more suitable in the different therapeutic applications in particular it improves the bio availability and reduce the bleeding risk associated to their use and other side effects.

Chemical and enzymatic modifications of the bacterial polysaccharide are described for example in the Italian patent N° IT1230785 where the K5 polysaccharide is N-deacetylated and N-sulphated; then it undergoes C5 enzymatic epimerization of the glucuronic acid. These transfers are followed by other transfers of enzymatic sulphation both on uronic acid and on the aminosugar.

The patent application WO92/17509 describes a method for heparin like products preparation starting from K5 polysaccharide by means of N-deacetylation, N-sulphation and C5 enzymatic epimerization passages, followed by chemical O-sulphation and optionally by a N-sulphation.

The patent application WO 96/14425 and the U.S. Pat. No. 5,958,899 describe a method for the preparation of K5 polysaccharide derivatives having high content of iduronic acid obtained by N-deacetylation and N-sulphation, enzymatic epimerization to iduronic acid of more than 50% of the glucuronic acid using modified buffers to obtain a critical viscosity, followed by sulphation of at least some of the free hydroxyl groups of the uronic acid and of the glucosamine groups.

The patent application WO97/433117 and the U.S. Pat. No. 6,162,797 describe the preparation of K5 derivatives with high anticoagulant and antithrombotic activities obtained by means of N-deacetylation and N— sulphation, enzymatic epimerization of the glucuronic acid, and by O-supersulphation and N-resulphation.

The patent application WO 98/42754 and the U.S. Pat. No. 6,197,943 and Naggi A. et al. Carbohydrate Research 336 (2001) 283-290, describe a methodology for the preparation of sulphated glycosaminoglycans including K5 polysaccharide derivatives having high antithrombotic in vitro activity, by means of solvolitic desulphation of supersulphated precursors and optional 6O-resulphation. The patent application WO 0172848 and WO 02/50125 describe a method of preparation of glycosaminoglycans derivative from K5 polysaccharide having high anticoagulant and antithrombotic activity. The process comprises the following passages: a) N-deacetylation b) N-sulphation c) enzymatic epimerization of the glucuronic acid in iduronic acid d) supersulphation e) partial chemical desulphation f) optional selective 6O-resulphation. The process is characterized by the use of a glucuronyl C5-epimerase enzyme in a truncated form, in solution or immobilized. Moreover, the patent application U.S. Ser. No. 09/732,026 and Li et al. J. Biol. Chem, vol 276, 213 (2001) 20069-20077 have led to the discovery of a new mouse gene for the expression of the C5-epimerase enzyme containing the additional sequence at the N-terminal end which allows the production of complete forms of the enzyme having higher activity/stability with respect to the former.

SUMMARY

The present invention refers to a process for the preparation of sulphated glycosaminoglycans derived from N-acetyl heparosan which comprises the following steps:

a) N-deacetylation and N-sulphation of a N-acetyl heparosan polysaccharide isolated from natural or recombinant bacterial source, b) enzymatic epimerization through the glucuronyl C5-epimerase enzyme, c) partial O-sulphation combined to a partial O-desulphation, d) partial 6O-sulphation e) N-resulphation further comprising an intermediate controlled depolymerization step carried out alternatively after step b), c) or d) and wherein such process is characterized by the fact that the partial O-sulphation in step c) is carried out using a molar ratio between the sulphating/hydroxyl agent of the N-acetyl heparosan lower than or equal to 5, more preferably lower than 2.5 or even more preferably lower than 1.5 and that the partial 6O-sulphation in step d) is carried out using a molar ratio between the sulphating/hydroxyl agent of N-acetyl heparosan equal to or lower than 2.

According to a preferred embodiment the intermediate depolymerization is carried out after the epimerization step b).

Both partial O-sulphation and partial 6O-sulphation are carried out with sulphating agents selected among: triethylamine-$SO_3$, trimethylamine-$SO_3$, pyridine-$SO_3$ in an aprotic polar solvent preferably non-donor of formyl groups, such as tetramethylene sulfone, 2,4-Dimethylsulfolane, N,N-Dimethylacetamide or N,N-diethylacetamide. Optionally the process comprises an affinity selection step on a matrix carrying antithombin III or its fragments.

The invention also concerns the sulphated glycosaminoglycans K5OS6OSNS-epi obtained according to the described process for pharmaceutical use. These products are characterized by a 6O-sulphation degree higher than 40% and preferably comprised from 50% to 85% very close to the values of extractive heparin and by the presence, at the reducing end, of an anhydromannitol residue, preferably sulphated in positions 1, 3 and 6. They are also characterized by a sulphation degree of the hydroxyl group in positions 1 and 6 of the anhydromannitol equal to or higher than 20% and according to a preferred aspect by the complete absence of formyl groups on the amino sugar.

According to the invention the sulphated glycosaminoglycans show a biological activity anti-factor Xa in plasma higher than that of the biotechnological heparins obtained according to prior art methods and a ratio between antiXa and anti IIa activity equal to or higher than 1, alike the extractive heparins.

The products obtainable according to the process of the invention:

a) are able to release a tissue factor inhibitor (TFPI) from the cells of the vascular endothelium just like the extractive heparins or even more, b) are particularly resistant to degradation with hydrolytic enzyme such heparinase I, c) are able to inhibit thrombin and Xa factor protease release, d) show a low affinity for the PF4 factor (platelet factor 4).

According to a further aspect, the invention refers to biotechnological heparins (modified N-acetyl heparosan) obtained according to the process of the invention for therapeutic use and to the pharmaceuticals compositions comprising such products as active principles. According to a further aspect the invention regards the use of the products obtained for the preparation of drugs with antithrombotic and anticoagulant heparin-like activities, for the preparation of profibrinolytic and anti-aggregant medicaments and for the preparation of medicaments for the prophylaxis and the treatment of thrombo-embolytic disorders caused by congenital or acquired lack of antithrombin III.

A further aspect of the invention concerns the preparation of O-sulphated, K5OSNH$_2$-epi and K5OS6OSNH$_2$-epi intermediates carrying the amminic group of the amino sugar free, preferably free from formyl groups wherein such intermediates can be isolated and used for the preparation of N-sulphated and/or N-acetylated heparosan derivatives.

DETAILED DESCRIPTION OF THE INVENTION

Figure 1:
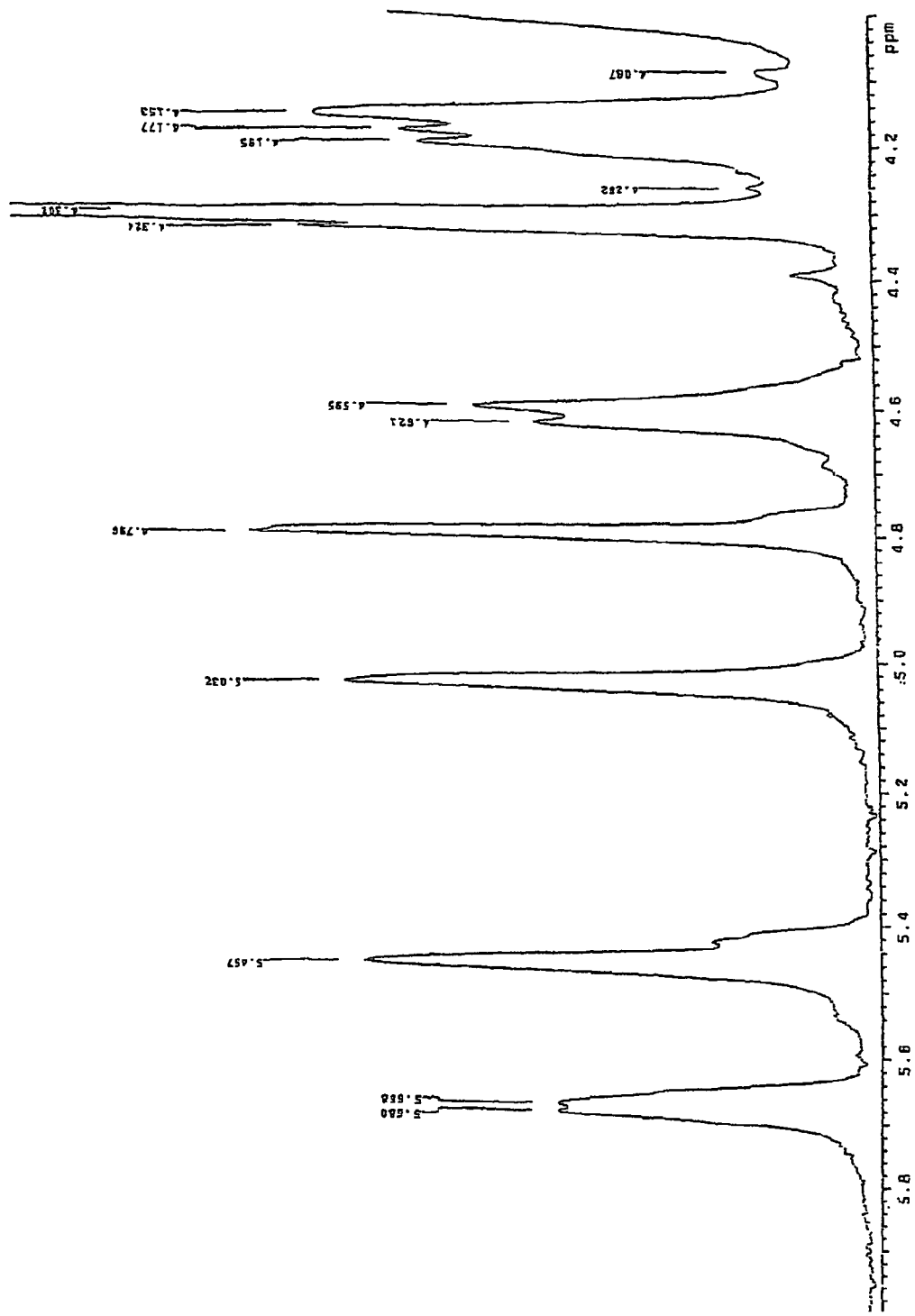
FIG. 1 spectrum $^1$H-NMR of the anomerical region of the polysaccharide K5 N-sulphated-epimerised as described in example 1.
Figure 2:
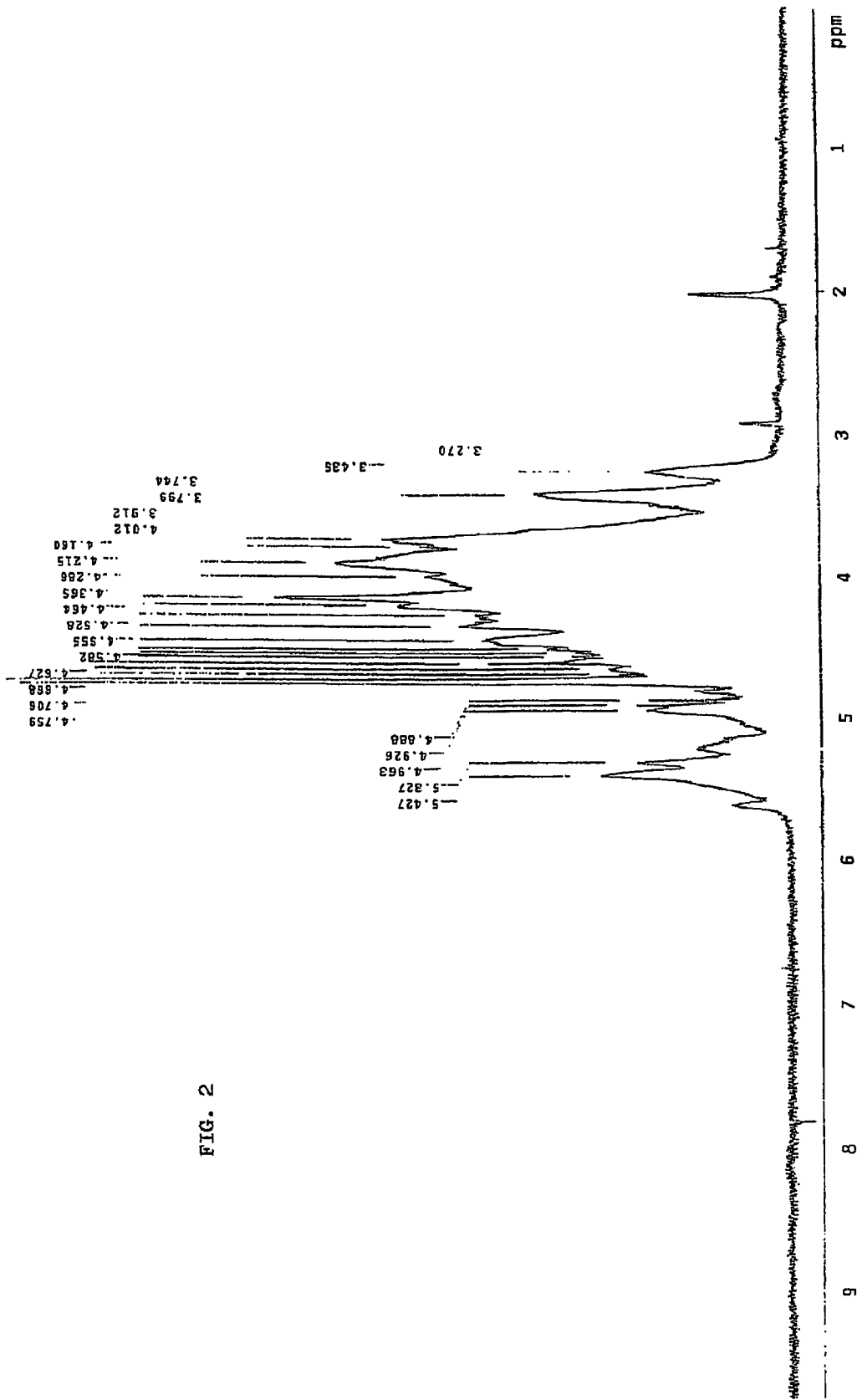
FIG. 2 spectrum $^1$H-NMR of the product obtained in example 1.

According to a main aspect, the invention is related to a process for the preparation of sulphated glycosaminoglycans derived from N-acetyl heparosan and called for the purpose of this invention, "Biotechnological Heparins", which comprises the following steps:
a) N-deacetylation and N-sulphation of a N-acetyl heparosan polysaccharide isolated from a natural or recombinant bacterial source,
b) enzymatic epimerization by a glucuronyl C5-epimerase enzyme,
c) partial O-sulphation combined to partial O-desulphation,
d) partial 6O selective sulphation,
e) N-resulphation, wherein this process further comprises an intermediate step of controlled depolymerization carried out alternatively after step b) or c) or d) and wherein said process is characterized by the fact the O-sulphations are partial, wherein in step c) this is achieved using a molar ratio between the sulphating agent and the substrate hydroxyl groups (epimerised N-acetyl heparosan) lower than or equal to 5, more preferably lower than or equal to 2.5 or, even more preferably, lower than or equal to 1.5 and a sulphation time lower than 10 hours. A partial 6O-sulphation according to step d) is obtained by using a molar ratio between the sulphating agent and the hydroxyl groups of the substrate (epimerised N-acetyl heparosan) lower than or equal to 2, or more preferably lower than or equal to 1.5 and sulphation time lower than 2 hours or, even more preferably lower than or equal to 90 minutes, or, even more preferably, lower than or equal to 60 minutes at a temperature comprised between 4° C. and 30° C., preferably between 10° C. and 25° C.

The partial O-sulphation according to step c) and the partial 6O-sulphation according to step d) are carried out with known sulphating agents in an aprotic polar solvent preferably non-donor of formyl groups, more preferably selected from: N,N-dialkylacetamide (more preferably N,N-Dimethylacetamide or N,N-diethylacetamide) and sulfolans (preferably tetramethylene sulfone or 2,4-Dimethylsulfolane).

The use of an organic solvent non-donor of formyl groups combined to partial sulphation conditions leads to products characterized by the lack of formyl groups or their derivatives on the amino sugar and to a distribution of sulphate groups similar to the one of extractive heparins.

According to the process of the invention, controlled depolymerization is carried out as an intermediate step, which means alternatively after step b), c) or d) and not in a final phase as described in the prior art. It is preferably carried out on the epimerised N-sulphated heparosan polysaccharide before or after step c) of partial O-sulphation. It can be carried out by physical methods including a gamma rays treatment or by chemical methods including a beta-gamma treatment with nitrous acid or its salts or a treatment with periodic salts or a free-radicals treatment. According to a preferred aspect, the depolymerising agent is nitrous acid and the polysaccharide is used in a quantity comprised from 1 to 100 mg salt/g of polysaccharide. The reaction is performed at a temperature comprised from 4 to 10° C. More preferably, controlled depolymerisation is carried out for less than 30 minutes in the presence of sodium nitrite and it is terminated by adding a molar excess of sodium borohydride.

The intermediate depolymerization allows to obtain a low molecular weight product, preferably with a molecular weight lower than or equal to 15,000 Da, more preferably comprised from 3,000 to 9,000 Da, carrying an anhydromannitol residue at the reducing end which shows, besides the hydroxyl sulphation in position 6, like in the extractive heparins, the hydroxyls sulphation in positions 1 and 3.

However the process is compatible also with a further depolymerization carried out at the end of the process. It has been observed that, when the depolymerization is carried out in an intermediate phase, the final products have anticoagulant and antithrombotic activity and a ratio between antiXa and anti IIa, unexpectedly higher than those found in products with the same molecular weight but obtained after a depolymerization performed after sulphation/desulphation and 6O-sulphation steps, as demonstrated by the data shown in table 1.

According to a preferred process embodiment, the N-acetyl heparosan polysaccharide is preferably derived from E. coli K5.

The process can further and optionally comprise a final phase of enrichment of the products resulting from steps a)-e), consisting in an affinity-chromatography on antithrombin III as described in Hook et al. FEBS Lett 1976, 66:90-93. N-deacetylation and N-sulphation are carried out according to prior art methods which comprise an alkaline hydrolysis performed at a temperature comprised from 30 to 80° C., preferably from 40 to 60° C., for a period of time comprised between 10 and 30 hours, preferably between 15 and 20 hours, followed by a treatment, for a time of up to 12 hours at 20-65° C. with a sulphating agent, preferably pyridine-sulphotrioxide in sodium carbonate.

The epimerization in step b) is carried out with the natural or recombinant glucuronyl C5-epimerase enzyme preferably in an immobilized form.

The enzyme is preferably the recombinant one described in WO98/48006 or even more preferably the one described in U.S. Ser. No. 09/732,026 and is preferably expressed and purified from insect cells or from yeast strains such as for example Saccharomyces Cerevisiae, Pichia methanolica, Hansenula polymorpha, Saccharomyces pombe, Kluyveromyces lactis, Kluyveromyces fragilis.

The enzyme immobilization is preferably carried out on resins CNBr Sepharose 4B (Pharmacia) or polymethacrylic or polystyrenic resins, with epoxidic groups or diolic groups activated with CNBr, in buffer $NaHCO_3$ 100-300 mM or in phosphate buffer 10-50 mM at pH 7.0-8.3, more preferably at pH 7.2-7.8, at a temperature of 4-25° for 12-72 hours.

According to a more preferred aspect, the epimerization reaction occurs at a temperature not higher than 35° C., preferably at a temperature comprised from 15 to 30° C., more preferably comprised from 20 to 25° C.

The epimerization is performed according to known methods, such as the ones described in WO 01/72848, preferably at a temperature not higher than 35° C., more preferably between 15 and 30° C., or even more preferably between 20° C. and 25° C.

The epimerization buffer is preferably a HEPES solution (preferably in concentration 25 mM) with pH comprised between 5.5-8.0, more preferably between pH 6.5-7.0, and further comprises the N-deacetylated and N-sulphated polysaccharide, EDTA 10-30 mM, preferably 15-25 mM, $CaCl_2$ (or alternatively salts of other divalent cations such as $Zn^{2+}$, $Ba^{2+}$, $Mg^{2+}$, $Mn^{2+}$,) in concentration comprised between 70 and 150 mM, much more preferably between 75-100 mM. The solution is thermostated at a temperature comprised between 15 and 30° C. (preferably 20-25° C.), preferably recycled at a flow of 30-240 ml/hour, for a time between 1 and 24 hours. The column contains preferably from $1.2 \times 10^7$ to $3 \times 10^{11}$ cpm equivalents of the immobilized enzyme on inert thermostated support.

The above defined operative conditions, in particular the preselected temperature, stabilize the C5-epimerase enzyme for thousand hours, allowing a remarkable saving of time and of the reagents for the preparation of the epimerization column. The partial O-sulphation in the process (step c) is performed by using known sulphating agents such as triethylamine-$SO_3$, trimethylamine-$SO_3$, pyridine-$SO_3$ in an aprotic polar solvent, preferably non-donor of formyl groups. It is performed using a molar ratio between the sulphating agent and the substrates hydroxyl groups lower than or equal to 5 or preferably lower than or equal to 2.5 or more preferably lower than 1.5, for a period of time equal to or lower than 10 hours, more preferably equal to or lower than 8 hours, preferably comprised from 1 to 6 hours at a temperature from 20 to 70° C., preferably from 30 to 60° C.

The partial O-sulphation is followed by a partial desulphation performed by treatment with a desulphating agent such as DMSO in methanol, for a period of time comprised from 10 to 240 minutes at a temperature comprised from 45 to 90° C.

Each process step can also comprise precipitations and/or intermediate polysaccharide desalifications according to known methods.

The partial 6O-sulphation (step d) is obtained by adding a sulphating agent in molar ratio with the substrate hydroxyl groups equal to or lower than 2 or preferably lower than 1.5 for a period of time equal to or lower than 2 hours, or preferably equal to or lower than 90 minutes, even more preferably between 4° C. and 30° C., preferably 10° C. and 25° C. in solution with an aprotic polar solvent, preferably non-donor of formyl groups. According to an alternative embodiment of the process, the partial 6O-sulphation (step d) is performed after the N-resulphation and steps d) and e) are performed in an inverted order.

The N-resulphation (step e) is preferably performed in carbonate buffer by adding a known sulphating agent, such as for example triethylamine-$SO_3$, trimethylamine-$SO_3$, pyridine-$SO_3$.

In conclusion, the process of the invention shows the following innovative elements: partial O-sulphation (O-sulphation and 6O-sulphation), depolymerization performed in an intermediate and not as a final step and, furthermore, a partial O-sulphation and 6O-sulphation performed in an aprotic polar organic solvent preferably non-donor of formyl groups.

The N-acetyl heparosan derivatives obtained from the process of the invention present characteristic structure and biological differences with respect to the biotechnological heparins obtained according to well-known prior art processes.

From a chemical point of view the polysaccharides of the invention are defined as a polysaccharidic chain mix represented by the following general formula (I)

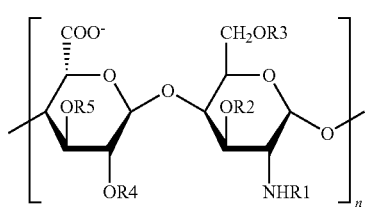

Formula (I)

where n ranges from 3 to 150, R1 can be a hydrogen, a group $SO_3^-$ or an acetyl group. R1 does not present other functional groups such as formyl groups. R2, R3, R4 and R5 can be hydrogen or a $SO_3^-$ group where preferably R1, R2, R3, R4, R5 are substituted as follows:

R1 from 85 to 97% with $SO_3^-$ groups and/or from 3% to 15% of acetyl groups and/or from 0 to 12% of $H^+$ R2 from 15 to 60% with $SO_3^-$ R3 with $SO_3^-$ groups to at least a 40%, preferably from 50% to 85% at least 20% of the glucuronic acid units are non sulphated in positions R4 and R5.

In particular the depolymerised polysaccharides according to the process of the invention, show at their reducing extremity an anhydromannitol residue with one or more of sulphated hydroxyl.

This occurs when the depolymerization is carried out in presence of nitrous acid or its derivatives, such as the sodium nitrite, followed by the sodium borohydride treatment, to obtain the compounds according to the following structure (II)

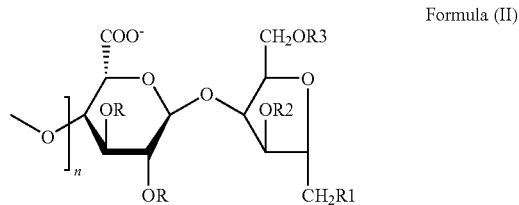

Formula (II)

where R1, R2, R3 can be hydrogen or a $SO_3^-$ group and preferably where:

R1 ranges from 0 to 100% of $SO_3^-$

R2 from 0 to 100% of $SO_3^-$

R3 from 0 to 100% of $SO_3^-$

Preferably R1 and R3 comprise from 20% to 85% of $SO_3^-$ and R2 from 15 to 60% of $SO_3^-$ The preferred products are those with a molecular weight lower than or equal to 15,000 Da, or preferably comprised from 1,500 and 15,000 Da, even more preferably from 3,000 to 9,000 Da.

The products obtained according to the invention are different from a structural point of view as compared to the products of the prior art, because of the presence of multiple signals in the $^{13}C$ NMR spectrum region comprised from ppm 79 to 89, in particular from 80 to 86 ppm, which are in excess with respect to the characteristic signals of the anhydromannitol (see FIG. 10 which shows the $^{13}C$ NMR spectrum at high resolution of the sample prepared in example 9) and which indicate the presence of anhydromannitol variously sulphated in particular on the hydroxyls in positions 1 and 6, in low molecular weight products prepared according to the process of the invention with an intermediate depolymerization.

More particularly the products obtained according the invention process are different because of sulphation of the hydroxyls in position 1 of the anhydromannitol as showed by the increase of the signal in the region at ppm 67-68 and by the decrease of the signal disappearance in a region at ppm 61-63 in spectrum $^{13}C$ NMR.

Figure 9:
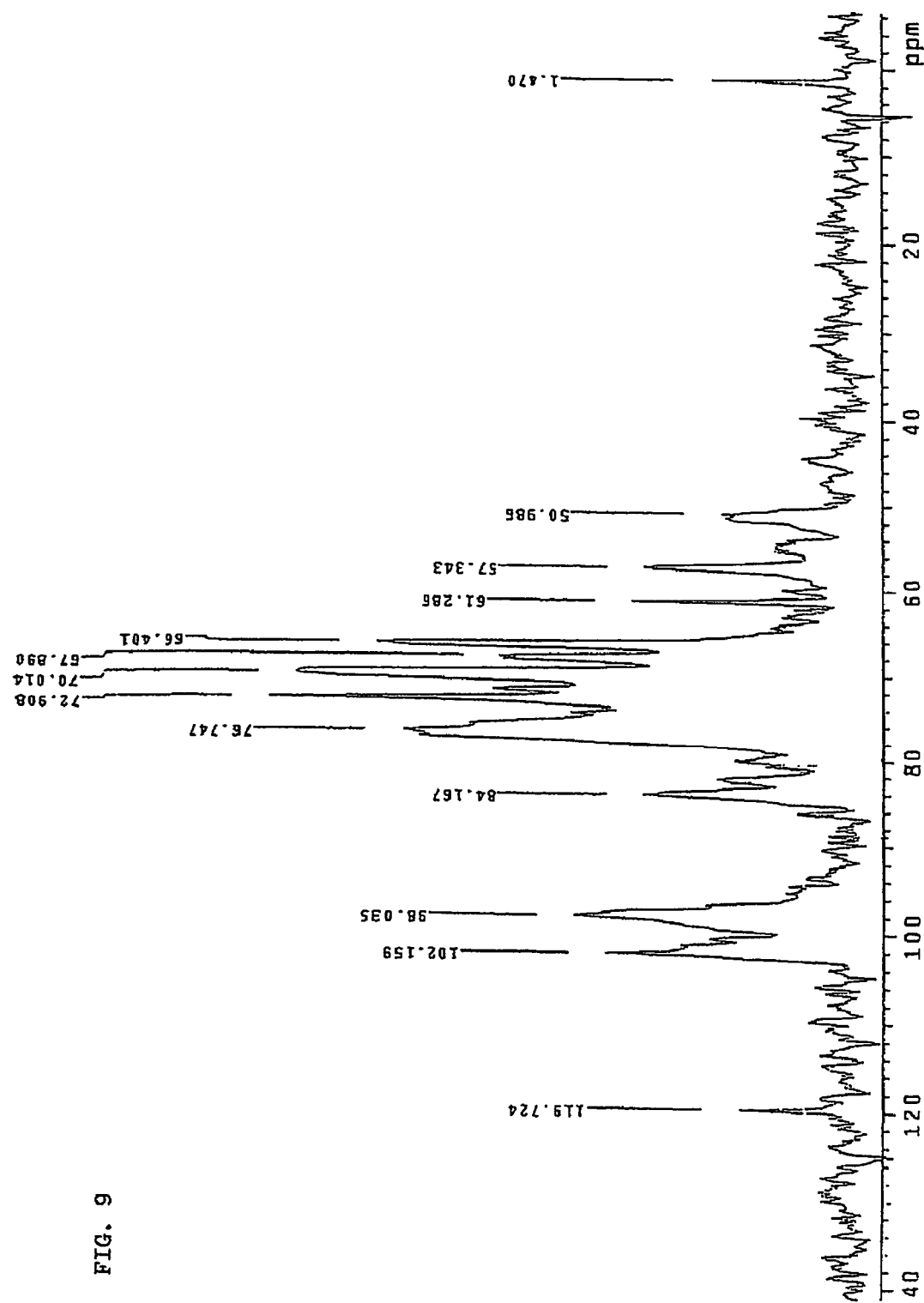
FIG. 9 spectrum $^{13}$C-NMR of the product obtained in example 8.
Figure 11:
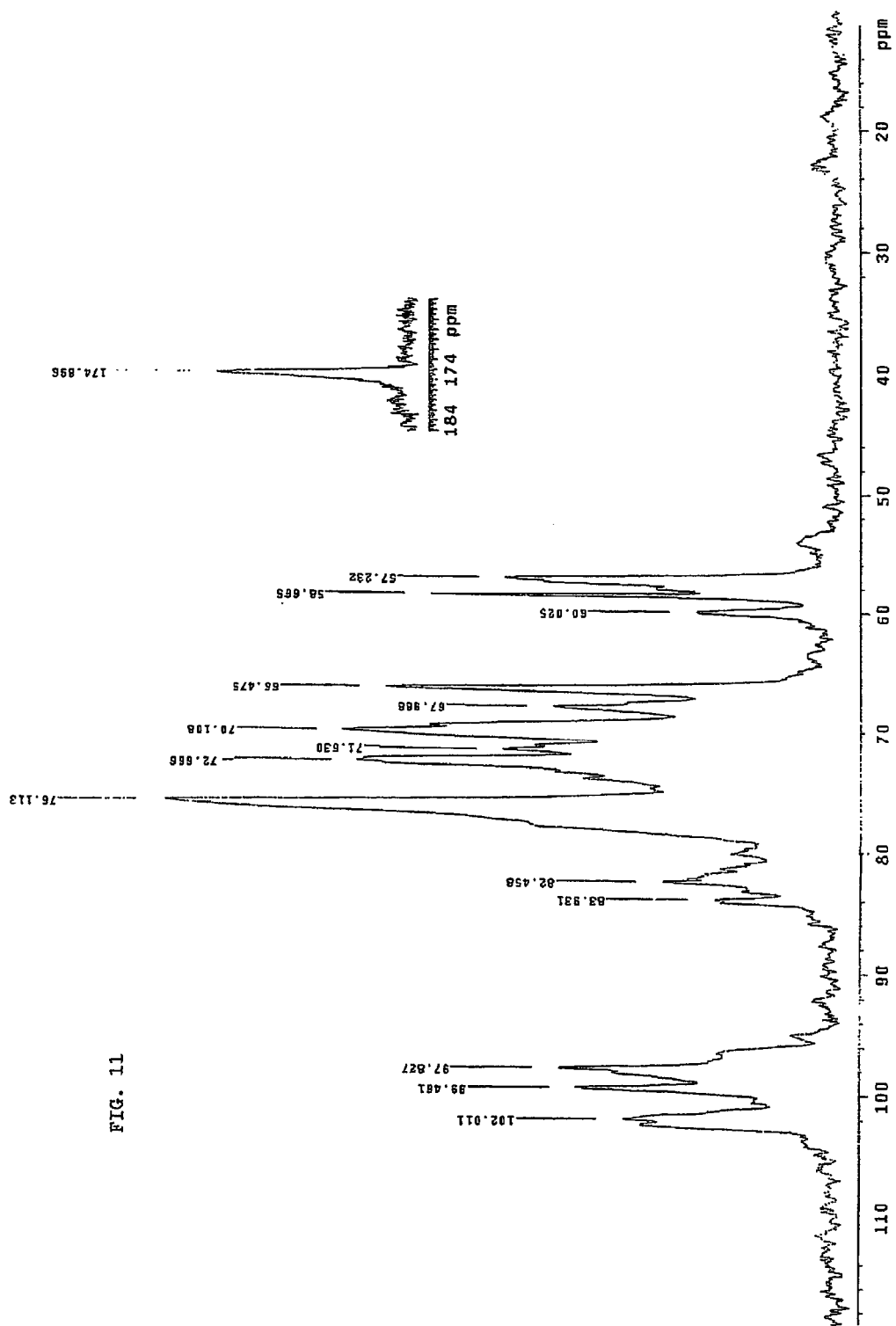
FIG. 11 spectrum $^{13}$C-NMR of the product obtained in example 10.
Figure 12:
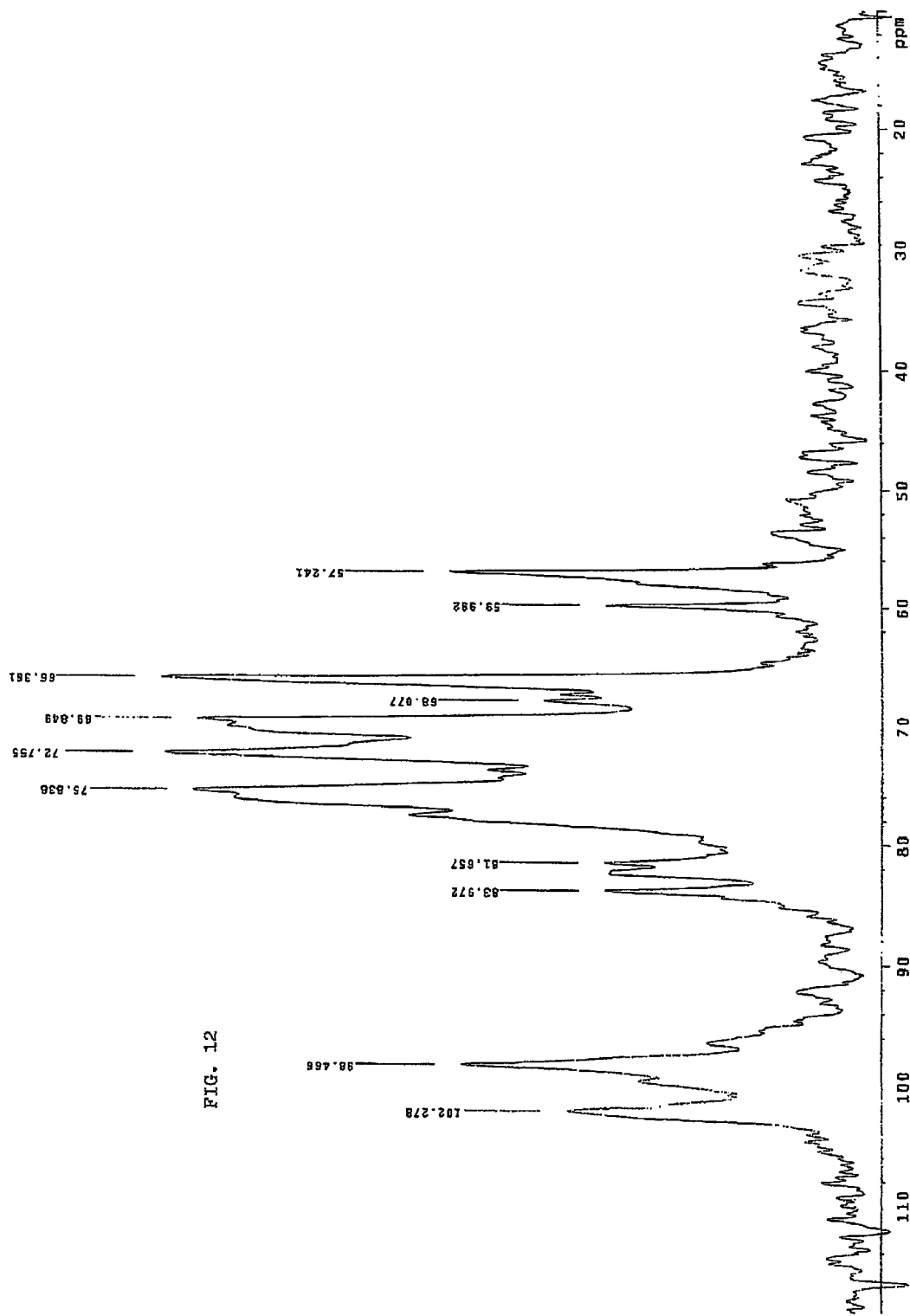
FIG. 12 spectrum $^{13}$C-NMR of the product obtained in example 11.

The difference is showed by comparing the spectrum of FIG. 11 (corresponding to the polysaccharide produced as described in example 10) and the one shown in FIG. 9 (polysaccharide produced as described in example 8). These differences are more evident by means of two-dimensional NMR according to the method described in Guerrini et al. Seminars in Thrombosis and Hermostasis, vol 27, 5, 473-482, 2001.

The main characteristic of these regions derives from the partial or total sulphation of the available hydroxyl groups of the anhydromannitol which are formed at the reducing end of the polysaccharide during depolymerization, when this is carried out before the sulphation step and in particular by the sulphation of the hydroxyls in positions 1 and 6.

A further characteristic of the products of the invention with respect to the products and procedure of the prior art (such as i.e. the ones showed in the experimental examples 6 and 7 comparative of the present application) is the absence of the signals at 7-9.5 ppm in the spectrum $^1H$ NMR and at 51 and 165 ppm in the spectrum $^{13}C$ NMR which indicates the absence of chemical groups different from a free aminic group or from an acetyl group or from the sulphate group on the glucosamine in all the products derived with low and high molecular weight.

On the contrary these signals are usually present in products derived from processes wherein sulphation of N-acetyl heparosan is performed in organic solvents donor of formyl groups such as N,N-dialkylformamide.

Sulphated glycosaminoglycans obtained according to this invention show an anticoagulant activity measured as anti-factor Xa in presence of plasma, higher than that of biotechnological heparins obtained according to known modification methods. Moreover, they show a ratio between antiXa and anti IIa activity equal to or higher than 1, very similar to the one of extractive heparins.

In particular the new products show:
a) a factor Xa inhibitory activity higher than 50 IU/mg, more preferably higher than 70 IU/mg in tests carried out in the presence of human plasma. The anti Xa factor activity is preferably measured as described in Ten Cate H et al. Clin. Chem 3,860-864 (1984) or in European Pharmacopoeia 1997 $3^{rd}$ edition. In the presence of plasma this biological activity is surprisingly higher than that of biotechnological heparins produced with prior art processes, and is similar to the one measured for extractive heparins with high or low molecular weight,
b) an activation capacity of the TFPI (Tissue Factor Pathway Inhibitor, described in Bronze G J Jr et al. Blood 71, 335-343, 1988)-equal to or higher than that of extractive heparins,
c) a ratio between anti Xa/anti IIa activities equal to or higher than 1 at comparable molecular weight. More preferably the ratio is higher than 1.5,
d) a resistance to heparinase I digestion equal to or higher than that of extractive heparins,
e) capacity to inhibit the thrombin and Xa factor protease release,
f) low affinity for the PF4 factor (platelet factor 4)

The activation ability of TFPI from vascular endothelial cells enhances the antithrombotic and antinflammatory activity of these products and extends and improves the therapeutic indications to deep venous thrombosis in chirurgical procedures, ischemic complications of the unstable angina and to myocardial heart attack and to ischemic events.

The ability to inhibit the protease production, combined to the increased TFPI production, allows the further extension of the therapeutic indications of these products to the treatment of sepsis and of its complications such as the disseminated intravascular coagulation (CID) and to the treatment of diseases caused by congenital or acquired lack of antithrombin III.

The determination of the activity on TFPI factor after treatment with the products of the invention is carried out for instance in Vitro on HUVEC cells according to the process described in Gori A M. Et al. Thromb. Haemostasis:81:589-593 (1999).

The N-acetyl heparosan derivatives obtained according to the invention (biotechnological heparins) are particularly resistant to degradation with hydrolytic enzymes such as the heparinase 1. This characteristic together with the possibility to obtain low molecular weight products that by itself increases the bioavailability and decreases the hemorrhagic risk associated to their use and the collateral effects with respect to high molecular weight heparins, together with a high Xa anti-factor activity and with a low sulphation degree, allows their use not only for the parenteral but also for the oral way of administration.

As before mentioned, the product obtained with the process invention shows the capacity to inhibit the thrombin protease generation and Xa factor.

The inhibition of protease generation is preferably carried out in fibrinogen-depleted plasma. The inhibition of both the thrombin (factor II) and the Xa factor generation is preferably monitored using an amidolytic method both for the intrinsic and extrinsic coagulation system.

According to both methods, in both the systems used, the products derived from the invention show a strong inhibition activity both of the thrombin and of the Xa factor and this characteristic improves the antithrombotic profile of these products. The products obtained according to the process of the invention are furthermore endowed with a low affinity for the PF4 factor (Platelet Factor 4) that can be measured in plasma as residual anti-Xa activity after adding a fixed quantity of PF4 factor in the solution containing the biotechnological heparins.

The residual anti Xa activity calculated as percentage with respect the initial activity is higher than the one obtained with extractive heparins or with extractive heparins with low molecular weight which indicates a lower affinity for PF4.

This lower binding affinity improves the clinical profile of the products obtained according to the invention as it decreases the risk of thrombocytopenia onset induced from heparin (HIT). Even if the preferred molecular weight of the obtainable products is lower than 15,000 Da, or is more preferably comprised from 3,000 to 9,000 Da, molecular weight products >15,000 Da are obtainable simply by changing the depolymerization conditions, still maintaining their biological properties such as the anti-Xa high activity, the heparinase resistance and the factor TFPI liberation.

In conclusion the biotechnological heparins produced according to the invention present the following main characteristics:
a region comprised from 79 to 89 ppm or more precisely comprised from 80-86 ppm by $^{13}C$ NMR characterized by the presence of multiple signals in excess with respect to the characteristic signals of the anhydromannitol and a signal increase at 67-68 ppm and/or a signal decrease or even disappearance at 61-62 ppm by $^{13}C$ NMR. These signals indicate the presence of variously sulphated anhydromannitol, in particular sulphated in positions 1, 3 and 6 and, even more particularly sulphated on the hydroxyl in position 1, as emphasized in the comparison between the spectra of FIG. 11 and of FIG. 9.
preferably the absence of signals at 7-9.5 ppm in a $^1H$ NMR spectrum and the absence of signal at 51 and 165 ppm in $^{13}C$ NMR spectrum which indicates the absence of formyl groups.
an anti-Xa (anticoagulant) activity in plasma higher than the one of biotechnological heparins prepared according to prior art methods.
an anti-Xa activity/anti IIa factor ratio equal to or higher than the one of biotechnological heparins prepared according to the prior art methods, preferably higher or equal to 1 or much more preferably higher or equal to 1.5.
a resistance to heparinase equal to or higher than extractive heparins;
the ability to inhibit thrombin and Xa factor production
low PF4 affinity The biological activities of the newly produced biotechnological heparins are peculiar: in particular a ratio between the anti-Xa activity and the anti-IIa activity equal to or higher than 1, it is usually in products obtained according to prior art is lower than 1 indicating an optimal ratio between the antithrombotic and anticoagulant activities which results from APTT values. Such ratio is similar to the one of extractive heparins.

An optimal characteristic also in respect to extractive heparins, evaluable from the high HCII values, is a better direct inhibition of thrombin, which implies the possibility to use the products of the invention in thrombo-embolytic and/or vascular disorders due to thrombin and in acquired or congenital lack of antithrombin III.

According to a further aspect the invention concerns the use of the products obtained according to the process described, alone or formulated in compositions with suitable pharmaceutically acceptable excipients or diluents, for the anticoagulant and antithrombotic treatment or the prophylaxis in substitution of extractive heparins and for the preparation of pharmaceuticals with profibrinolytic and antiaggregating activity.

Particularly suitable is the use of the invention products or of compositions comprising such products as the active ingredient for the prophylaxis and the treatment of unstable angina, myocardial heart attack, deep venous thrombosis, lungs embolism, ischemic events as well as for the treatment of sepsis and for the prevention of its complications such as disseminated intravascular coagulation (CID).

According to a further aspect the invention concerns the use of the invention products for the preparation of pharmaceuticals for the prophylaxis and treatment of unstable angina, arterial thrombosis, atherosclerosis and for the treatment of thromboembolic diseases due to congenital or acquired lack of antithrombin III.

The products can be carried by micelles, carrier molecules etc. and result particularly suitable for oral use besides for the parenteral one.

Therefore it represents a further aspect of the invention the pharmaceutical compositions containing as the active principle the polysaccharides derivatives of the N-acetyl heparosan produced according to the process of the invention, in appropriate formulations both for the oral and the parenteral use.

According to a further aspect the invention concerns the preparation of O-sulphated intermediates with the free amminic group of the amino sugar and completely lacking formyl groups and without any of anticoagulant activity, useful, for example, in the preparation of the final products of the invention.

Particularly preferred is the intermediate K5-OS,NH$_2$,epi obtained and isolated according to the process described in this invention, which is defined as a mixture of polysaccharidic chains represented by the following general formula (III):

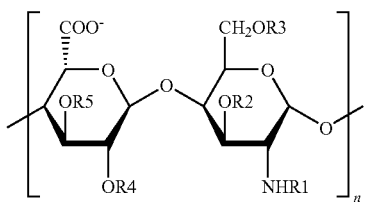

Formula (III)

where n ranges from 3 to 150, R1 can be hydrogen or an acetyl group with an acetylation degree ranging from 3% to 15%.

R1 does not carry any other functional groups, preferably it does not carry formyl groups; R2, R3, R4 and R5 can be hydrogen or a SO$_3^-$ group wherein sulphation range is preferably comprised from 30% to 98%.

K5OSNH$_2$-epi, ($^1$H NMR spectrum shown in FIG. 16) has a molecular weight preferably comprised between 1,500 and 15,000 Da or, more preferably from 3,000 to 9,000 Da and is characterised by an anticoagulant activity lower than 10 IU/mg as measured by the anti factor Xa activity with a chromogenic method (Coatest Heparin kit, Chromogenix).

K5OSNH$_2$-epi is useful, for example, in the preparation of the products of the invention.

K5-OS6OSNH$_2$,epi is obtained and it can be isolated according to this invention is defined as a mixture of polysaccharidic chains represented by the following general formula (IV):

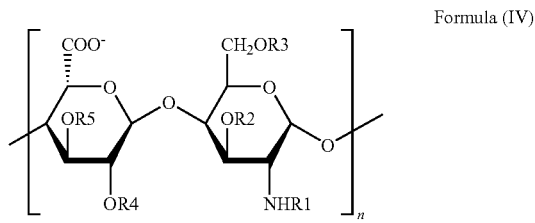

Formula (IV)

where n ranges from 3 to 150, R1 can be hydrogen or an acetyl group where the acetylation range is comprised from 3% to 15%. R1 preferably does not carry other functional groups. Preferably it does not carry formyl groups.

R2, R3, R4 and R5 can be hydrogen or a SO$_3^-$ group where R2, R3, R4, R5 are preferably substituted as follows:

R2 from 15 to 60% of SO$_3^-$

R3 higher than 40%, preferably from 50 to 85% of SO$_3^-$ and at least 20% of glucuronic acid units are not sulphated in positions R4 and R5. K5-OS6OSNH$_2$-epi intermediate, ($^{13}$C NMR spectrum shown in FIG. 15) has a molecular weight preferably comprised from 1,500 to 15,000 Da or more preferably from 3,000 to 9,000 Da. The K5-OS6OSNH$_2$-epi intermediate is characterized by a free aminic group on the amino sugar, non sulphated and preferably free from formyl groups. It is also characterized by an anticoagulant activity lower than 10 IU/mg as found by measurement of the anti factor Xa activity with a chromogenic method (Coatest heparin kit, Chromogenix). The K5-OS6OSNH$_2$,epi intermediate is useful, for example, in the preparation of N-sulphated derivatives according to the invention and it does not have any anticoagulant activity.

In a particularly preferred embodiment the process for the production of the bioheparins from bacterial polysaccharides, such as the N-acetyl heparosan (K5 polysaccharide of *E. coli*) comprises the following steps:

Preparation and Purification of N-acetyl Heparosan Polysaccharides

The starting material is preferably the N-acetyl heparosan polysaccharide represented by a chain of the disaccharidic units [-4)-GicA α 1-4 GlcNAc-(1-]$_n$ constituted by a D-glucuronic acid and a N-acetyl glucosamine monomers linked by β 1-4 bonds. The polysaccharide can be obtained for example from natural *Escherichia coli* K5 strain (strain Bi 83337/41 serotype O10:K5:H4) (in this case the polysaccharide is the K5 polysaccharide) or from *Pasteurella multocida* bacteria type D, or from their derivatives or mutants or *Escherichia coli* recombinant strains obtained for example as described in Finke A, et al. Journal of Bacteriology, 173 (13): 4088-4094, 1991, or in Drake C R, Roberts I S, Jann B, Jann K and Boulnois G J. FEMS Microbiol Lett. 54 (1-3): 227-230, 1990.

The *Escherichia coli* strain useful for the production of K5 polysaccharide can be obtained also from public collections of microorganisms such as ATCC (American Type Culture Collection-USA) n° ATCC 23506.

*Pasteurella multocida* type D stock can be obtained from ATCC collection (ATCC n° 12948).

The N-acetyl heparosan polysaccharide is obtained by microbial fermentation and extraction from the culture broth. The purification is performed by known techniques, as those described for example in patent WO 01/02597 in which is used the following culture broth: skimmed soya flour 2 g/l, $K_2HPO_4$ 9.7 g/l, $KH_2PO_4$ 2 g/l, $MgCl_2$ 0.11 g/l, sodium citrate 0.5 g/l, ammonium sulfate 1 g/l, glucose (sterilized apart) 2 g/l, water up to 1,000 ml, pH 7.3.

A pre-culture is preferably inoculated with a cell suspension of *E. coli* Bi 8337/41 (O1O:K5:H4) derived from a slant kept in Tryptic soy agar. It is incubated at 37° C. for 24 hours under stirring. In a subsequent step a fermentor containing the cited medium, is inoculated at 0.1% with the above mentioned pre-culture and a fermentation for 18 hours at 37° C. is carried out. During fermentation the pH, oxygen, residual glucose, produced K5 polysaccharide and bacterial growth are monitored.

At the end of fermentation the temperature is brought to 80° C. for 10 minutes. The cells are separated from medium through centrifugation at 10,000 rpm and the supernatant is filtered through filtration membranes with a 1,000-10,000 Da cut-off to reduce the volume to about ⅕. The K5 polysaccharide is, then, precipitated by adding 4 volumes of acetone and recovered by centrifugation.

Deproteinization of the pellet is preferably carried out using a protease type II from *Aspergillus oryzae* in a buffer comprising NaCl 0.1 M and EDTA 0.15 M at pH 8 containing SDS at 0.5% at 37° C. for 90 minutes.

The solution is ultra-filtered with 10,000 Da cut-off membranes and the polysaccharide is then precipitated with acetone. The purity of the polysaccharide is usually above 80% and is measured by at least one of the following analytical methods: calculation of uronic acids (carbazole method) proton and $^{13}C$—NMR, UV and/or protein content.

a) N-deacetylation and N-sulphation of a N-acetyl heparosan polysaccharide from microbic source.

A quantity preferably comprised from 5 to 10 g of purified K5 polysaccharide is solubilized in 200-2,000 ml of 2N sodium hydroxide and left to react at 40-80° C. until deacetylation is completed (i.e. 15-30 hours). The solution is led to neutrality.

The solution containing the deacetylated K5 polysaccharide is maintained at 20-65° C. and 10-40 g of sodium carbonate are added in a single step as well as with 10-40 g of a sulphating agent selected among reagents such as pyridine-sulphotrioxide adducts, trimethylamine-sulphotrioxide, etc.

The sulphating agent is added in a time of up to 12 hours. At the end of reaction, if necessary, the solution is brought to room temperature, and to a pH comprised from 7.5 to 8.

The product is purified from salts by known techniques such as, for example, by diafiltration with spiral membranes 1,000 Da (prep-scale cartridge-Millipore). Retained product is reduced in volume until a 10% polysaccharide concentration is obtained. Concentrated solution, if necessary, can be exsiccated with known methods.

The N-sulphated/N-acetyl ratio is measured with $^{13}C$-NMR.

b) Enzymatic Epimerisation by Glucoronyl C5-Epimerase.

The C5 epimerization step, which involves the epimerization of a part of the glucuronic acid in iduronic acid, is carried out with the glucuronyl C5-epimerase enzyme (called C5-epimerase) natural or recombinant either in solution or preferably in an immobilized form.

For this step, recombinant C5-epimerase enzyme as described in WO 98/48006 is used. Preferably, the recombinant enzyme modified as described in U.S. Ser. No. 09/732, 026 and in Li et al J. Biol. Chem, vol 276, 23, (2001) 20069-20077) and contains an additional sequence at its N-terminal end.

The recombinant enzyme is preferably expressed and purified from insect cells or yeast cells preferably belonging to the genera of *Saccharomyces cerevisiae, Pichia pastoris, Pichia methanolica, Hansenula polymorpha, Saccharomyces pombe, Kluyveromyces lactis, Kluyveromyces fragilis.* b.1) Immobilization of the C-5 epimerase on resins.

The recombinant enzyme can be immobilized on different inert matrices such as resins, membranes or glass beads derivatized with functional groups by known techniques such as cyanogen bromide, glutaraldehyde, carbodiimide or by letting the enzyme react with a ionic exchange resin or by letting it absorb on membranes.

According to a preferred realization the enzyme is immobilized on commercial resins such as CNBr Sepharose 4B (Pharmacia) or on polystyrenic or polymethacrylic resins (Resindion Mitsubishi) with epoxidic or diolic-CNBr activated groups.

Particularly preferred according to the invention is the enzyme immobilization on polymethacrylic resin with diolic groups activated with CNBr in buffer $NaHCO_3$ 100-300 mM at 7.0-8.3 pH, preferably 7.2-7.8 pH at a temperature of 4-25° C. for 12-72 hours.

According to the invention, the binding reaction of the enzyme to the inert matrix is carried out in the presence of K5 N-deacetylated N-sulphated substrate to avoid such binding to involve the enzyme active site with loss of activity.

Measure of the immobilized enzyme activity is carried out by letting recirculate, through a column containing the immobilized enzyme, the quantity of N-deacetylated N-sulphated K5 theoretically convertible by cpm of the immobilized enzyme, dissolved in buffer HEPES 25 mM, KCl 0.1 M, Triton X100 0.01% and EDTA 0.15 M at 7.4 pH at 37° C. for 24 hours with the flux of 0.5 ml/minute. After purification through DEAE chromatographic method and desalting on Sephadex G-10, the product is lyophilised and analysed for the iduronic acid content by proton NMR technique according to WO 96/14425.

b.2) Epimerisation with Immobilised Enzyme.

The C5 epimerisation reaction can be performed, for example, as described in WO 96/14425 in reaction buffer at pH 7.4 comprising preferably HEPES 0.04 or Tris 0.05 M, KCl 0.4 M, EDTA 0.06 M and triton X-100 and one or more additives such as, in particular, glycerol or polyvinylpyrrolidone.

The reaction can be performed as described in WO 01/72848 wherein a solution containing HEPES 25 mM, $CaCl_2$ 50 mM at 7.4 pH, at a temperature of 30-40° C. is used.

Particularly preferred, are the reaction conditions of temperature and buffer which allow the activity of glucoronyl C5-epimerase to be long-lasting and stable even after immobilization on a column.

20-1,000 ml of an aqueous solution comprising 0.001-10 g of N-deacetylated N-sulphated K5 and EDTA 10-30 mM, preferably 15-25 mM, HEPES 25 mM, $CaCl_2$ in concentration from 70 to 150 mM (preferably 75-100 mM) at pH 5.5-8.0, preferably pH 6.5-7.0 and thermostated at a temperature comprised from 15° C. to 30° C. (preferably 20-25° C.) are allowed to circulate at a flux of 30-240 ml/hour for a time comprised from 1 to 24 hours in a column containing from $1.2 \times 10^7$ and $3 \times 10^{11}$ equivalents of the enzyme immobilized on a thermostatic inert medium at a temperature comprised form 15° C. to 30° C., preferably from 20 to 25° C.

The above temperature and buffer condition increase the enzyme stability on column for a working period longer than 3,000 hours and, therefore, make the process particularly advantageous. At the end of reaction the sample is purified by passing through a DEAE resin or a Sartobind DEAE cartridge and precipitated by addition of 2M of NaCl and, finally desalted on G10 Sephadex resin (Pharmacia) or purified through precipitation with 2 volumes of ethanol and passing on IR 120H+ resin to obtain the sodium salt.

The product obtained under said preferred conditions has an epimerisation rate measured by proton NMR technique as described under WO 96/14425, of at least 50% (iduronic acid rate on total uronic acids).

Controlled Depolymerization.

The product obtained under step b) or c) or d) undergoes controlled depolymerization with known techniques such as deamination with nitrous acid as described in WO 82/03627, or by an oxidative opening with sodium periodate (EP 287477), or by free radicals treatment (EP 121067) or by beta-elimination (EP40144), or by gamma rays treatment (U.S. Pat. No. 4,987,222) to obtain molecular weight fractions preferably comprised from 1,500 to 15,000 Da, or even more preferably comprised from 3,000 to 9,000 Da.

According to a preferred aspect of the invention, controlled depolymerization is carried out before the sulphation steps.

In particular, the product resulting from the former steps is put under controlled depolymerisation with nitrous acid or with sodium nitrite. In this case the salt quantity used is comprised from 1 to 100 mg for each gram of polysaccharide, followed by reduction by borohydride in excess.

According to a second preferred embodiment, the sample is dissolved in 50-250 ml of water at 4° C. ad acidified with 1N hydrochloric acid A sodium nitrite quantity comprised from 5 to 500 mg is then added and the reaction is continued for less than 60', preferably less than 30'.

After destruction of the sodium borohydride in excess, the product is recovered by precipitation with 3 ethanol volumes and exsiccated in a vacuum oven. When depolymerization is carried out at the end of the process, it can be performed as described for example in WO 01/72848.

c) Partial O-Sulphation Combined with Partial O-Desulphation.

The product derived from the steps above is re-suspended in water at a concentration of 10%. The solution is cooled down at 10° C. and passed while keeping the temperature at 10° C. through a IR-120H+ cationic exchange resin. After the solution is passed through the resin is washed with deionised water until the eluate pH is higher than 6. The acidic solution is led to neutrality by adding a tertiary ammine or a quaternary ammonium salt such as a 15% tetrabutylammonium hydroxide aqueous solution obtaining the relevant ammonium salt. The solution can be concentrated to a minimum volume and lyophilised.

The product obtained is suspended in 10-1,000 ml of an organic solvent consisting, preferably of sulfolane or 2,4-dimethylsulfolane. Alternatively, the organic solvent can be N,N-dimethylformamide (DMF) or dimethylsulfoxide (DMSO) or N,N-dimethylacetamide. This organic solvent is added with a sulphating agent such as a pyridine-$SO_3$ adduct in solid form or in solution with the same solvents previously used.

The molar ratio between the sulphating agent and the polysaccharidic substrate (epimerised N-sulphated K5), to be intended as the ratio between the sulphating agent and the hydroxyl moles of the polysaccharidic dimer, is maintained equal to or lower than 5 or, more preferably, lower than 2.5 or, even more preferably lower than 1.5.

The solution is maintained at a temperature comprised from 20 to 70° C., preferably comprised from 30 to 60° C. for a period of time lower than or equal to 10 hours, more preferably equal to or lower than 8 hours, or even more preferably, equal to or lower than 6 hours. At the end of reaction the solution is eventually cooled down at room temperature and added with acetone saturated with sodium chloride till complete precipitation of the polysaccharide.

The precipitate is separated from the solvent by filtration, solubilized with the minimum quantity of deionised water and added with sodium chloride until a 0.2 M solution is obtained. The solution is brought to pH 7.5-8 by 2N sodium hydroxide addition. Acetone is then added to complete precipitation. The precipitate is separated from solvent by filtration. The obtained solid is solubilized with 10-100 ml of deionised water and purified from residual salts through ultrafiltration.

An aliquot is lyophilised for the structural analysis of the partially O-sulphated product by $^{13}$C-NMR and $^{1}$H-NMR.

The solution containing the partial sulphated product is passed through a IR-120+ cationic exchange resin or equivalent.

The resin is washed with deionised water until the pH of the eluate is higher than 6 and is then added with pyridine. The solution is concentrated to a minimum volume and lyophilised. The product is treated with 20-200 ml of a solution of DMSO/methanol (9/1 V/V) and the solution is kept at 45-90° C. for 10-420 minutes.

At the end the solution is added with 10-200 ml of deionised water and treated with acetone saturated with sodium chloride to complete precipitation.

The solid obtained is purified through diafiltration according to known techniques and an aliquot is lyophilised for structural analysis by $^{13}$C-NMR.

d) Partial 6O-Sulphation

The product from the previous step is then 6O-sulphated. The content of sulphate groups in 6O position is measured by known techniques such as for example NMR according to the conditions described in Guerrini et al. Seminars in Thrombosis and Hemostasis, vol 27, 5, 473-482, 2001.

The product obtained is resuspended in water at a concentration comprised from 5 to 10% and kept at room temperature. The solution is then passed through a resin having IR-120H+ cationic exchange or equivalent. After the solution flow, the resin is washed with deionised water and led to neutrality with a tertiary ammine or a quaternary ammonium salt such as, for example, tetrabutylammonium hydroxide in aqueous solution obtaining the relevant ammonium salt. The solution is concentrated to a minimum volume and lyophilised.

The product obtained is suspended in 10-1,000 ml of an organic solvent consisting N,N-dimethylformamide preferably, in sulfolane or in 2,4-dimethylsulfolane or in N,N-dimethylacetamide and added with a sulphating agent such as pyridine-$SO_3$ adduct in solid form or in solution with the same solvent.

The suspension is brought to a temperature comprised from 4° C. to 30° C., preferably from 10 to 25° C., treated with quantity of a sulphating agent such as the pyridine-$SO_3$ adduct using less than 2 equivalents compared to the hydroxile groups to be sulphated or even more preferably with less than 1.5 equivalents for 10-90 minutes and treated with acetone saturated by sodium chloride in such a quantity to complete precipitation. The obtained solid is then purified by diafiltration according to methods well known in the art. An aliquot is lyophilised for the structural analysis by $^{13}$C-NMR.

e) N-resulphation

The solution from step d) containing the 6O-sulphated polysaccharide, is brought to 20-65° C. and added with 10-100 g of sodium carbonate with a single addition and with 10-100 g of a sulphating agent selected among available reagents such as, preferably, the pyridine-sulphotrioxide The addition of the sulphating agent is carried out during a variable time up to 12 hours. At the end of the reaction, if necessary, the solution is brought to room temperature, and to a pH comprised from 7.5 to 8, preferably with 2M sodium hydroxide.

The product is purified from salts by known techniques such as, for example, dialfiltration using a spiral membrane of 1,000 Da (i.e. prep-scale cartridge-Millipore). The process is complete when the permeate conductivity is below 1,000 µS, preferably below 100 µS. The product obtained is reduced in volume till a polysaccharide concentration of 10% is obtained by filtration. An aliquot of the concentrated solution is lyophilised for structural analysis by $^{13}$C-NMR.

The 6O selective sulphation and N-resulphation carried out as described in this step, on products derived from step e) can be performed in a different order for example the N-resulphation at first and then the 6O-sulphation) as described in WO 98/42754, without modifying the biological activities of the final product.

Enrichment in Sequences Binding the Antithrombin III (Optional).

The product obtained as described in the previous step can be optionally further purified by chromatography for example on an anionic exchange chromatographic column such as for example on DEAE columns as described in Lam L. H. et al. Bioch. And Biophysical Research Communication vol 69, 2, pag. 570-577, 1976. Alternatively to this purification or besides this, the product can be subjected to a further affinity chromatography on columns carrying the whole or the partial human antithrombin sequence as described, for example, in Hook et al FEBS Lett 1976, 66:90-93 or in U.S. Pat. No. 4,692,435 or peptide sequences having a high affinity for heparin as described in Liu S et al. Proc. Natl. Acad Sci USA 1980, 77:6551-6555. This treatment allows the separation, by subsequent elution with a NaCl saline solution of at least a fraction able to bind to the solid phase.

In practice, 10-50 mg of product derived form the N-resulphation step are loaded on an affinity column where 50-100 mg of human antithrombin III are immobilized (Kedrion SpA, Lucca, Italia) in buffer Tris-HCl 10 mM at 7.4 pH and 0-0.15 M NaCl 4° C. The column is then washed with at least 3 volumes of buffer Tris-HCl 10 mM 7.4 pH.

The molecules bound with higher affinity to the column are eluted by Tris HCl 10 mM 7.4 pH containing from 0.5 to 3 M of NaCl.

The eluted material is, then, preferably diafiltered by 1,000 Da cut-off spiral membranes to eliminate salts and concentrated by lyophilization.

An aliquot can be analyzed by the Carbazole method, HPLC, NMR and chromogenic test to measure the antiXa activity.

The obtained material shows a greater antiXa activity enriched from 1.5 to 3 times the activity of the starting material.

The same increase in anti-Xa activity is obtained by treating the same way extractive heparins. This is a further signal of the likeness of the biotechnological heparins obtained according to this invention to extractive heparins, in binding to antithrombin III.

EXPERIMENTAL PART

Example 1

Biotechnological Heparin Production According to the Invention Process

The following steps have been followed:
a) N-acetyl heparosan polysaccharide preparation starting from *Escherichia coli* K5
b) N-deacetylation/N-sulphation
c) Epimerization
d) Depolymerization
e) partial O-sulphation/partial O-desulphation
f) partial 6O-sulphation
g) N-resulphation a) Polysaccharide Preparation N-acetyl heparosan polysaccharide was obtained through fermentation of *E. coli* Bi 8337/41 stock, serotype O10:K5:H4 (ATCC 23506) and subsequent extraction from culture broth and purification according to the description in patent WO 01/02597 using the following culture broth: skimmed soy flour 2 g/l, $K_2HPO_4$ 9.7 g/l, $K_2HPO_4$, 2 g/l $MgCl_2$ 0.11 g/l, sodium citrate 0.5 g/l, ammonium sulphate 1 g/l, Glucose (sterilized aside) 2 g/l, water up to 1000 ml, pH 7.3.

The culture was inoculated with a cell suspension derived from a slant kept in Triptic soy agar at 37° C. for 24 hours under stirring. The inoculum in fermentor, type F5 (industrie Meccaniche di Bagnolo SpA) containing the same abovementioned medium, was inoculated at 0.1% with the abovementioned Erlenmeyer flask culture and the fermentation was performed at the temperature of 37° C. for 18 hours. During fermentation were measured the pH, oxygen, residual glucose, produced K5 polysaccharide and bacterial growth. At the fermentation end, the temperature was taken to 80° C. for 10 minutes. The cells were separated from medium through centrifugation at 10,000 rpm and the supernatant filtered using filtration membranes with 10,000 Da cut-off to reduce volume to ⅕. The K5 polysaccharide was precipitated by adding 4 volumes of acetone and, finally, recovered by centrifugation.

Deproteinization of the solid obtained was performed by protease type II from *Aspergillus oryzae* in buffer of NaCl 0.1 M and EDTA 0.15 M at pH 8 containing 0.5% SDS, 37° C. for 90 minutes.

The solution obtained was ultrafiltered with membranes having a nominal cut-off of 10,000 Da and the polysaccharide was precipitated with acetone. The polysaccharide purity was measured by uronic acids determination (Carbazole method), $^1$H, $^{13}$C-NMR, UV and protein content.

b) N-deacetylation/N-sulphation 10 g of the product obtained from step a) was solubilized in 200 ml of 2N sodium hydroxide and left at 50° C. for 18 hours. The solution was brought to neutral pH with 6N hydrochloric acid. A N-deacetylated polysaccharide was obtained.

The N-deacetylated polysaccharide solution was kept at 40° C. and added with 10 g of sodium carbonate in a single addition and 10 g of pyridine-sulphotrioxide adduct in 10 minutes. The product obtained made up of N-deacetylated N-sulphated K5 polysaccharide, was purified from salts by diafiltration using a spiral membrane of 1,000 Da (prep-scale cartridge-Millipore). The purification process was completed when the permeate conductivity was below 100 µS.

The product was brought to a 10% polysaccharide concentration using the same diafiltration method and was then lyophilized.

The N-sulphate/N-acetyl ratio of the obtained product was 9.5/0.5 as measured through $^{13}$C-NMR.

c) Epimerization c-1) C5-Epimerase Immobilization On Resin.

5 mg of recombinant glucuronyl C5-epimerase obtained according to U.S. Ser. No. 09/732,026 and to Li et al J. Biol. Chem., vol 276, 23, (2001) 20069-20077, were dissolved in 200 ml of buffer Hepes 0.25 M, 7.4 pH, containing KCl 0.1 M, Triton X-100 0.1% and EDTA 15 mM, 100 mg of N-deacetylated N-sulphated K5 obtained according to the description in step b) were added to the solution. The solution was diafiltered in a 30,000 Da membrane at 4° C. till N-deacetylated N-sulphated K5 disappeared in diafiltered. To the solution retained by the membrane the buffer was changed by diafiltration and substituted with NaHCO$_3$ 200 mM at 7 pH and after concentration to 50 ml we added 50 ml of CNBr Sepharose 4B activated resin, which was left to react overnight at 4° C.

At the end of reaction the residual enzyme quantity in supernatant was measured with the Quantigold method (Diversified Biotec) after decantation. The enzyme in supernatant was absent, demonstrating that, with the method described, the enzyme was immobilized at 100%. To occupy the resin sites left available, the resin was washed with tampon Tris-HCl 100 mM at 8 pH.

For the measurement of the immobilized enzyme activity, a quantity of the immobilized enzyme theoretically corresponding to 1.2×10$^7$ cpm, was loaded in a column. In the column so prepared, 1 mg of N-deacetylated N-sulphated K5 obtained according to step b) was treated and dissolved in buffer HEPES 25 mM, KCl 0.1M, EDTA 0.015M, Triton X-100 0.01% at 7.4 pH, allowing it to recirculate through said column at 37° C. overnight with a flux of 0.5 ml/minute.

After purification by DEAE chromatography method and desalification on Sephadex G10, the sample was lyophilized and analyzed for the iduronic acid content through proton NMR technique according to the description on patent WO 96/14425.

c-2) Epimerization With Immobilized Enzyme.

10 g of N-deacetylated N-sulphated K5 polysaccharide were dissolved in 600 ml of EDTA 15 mM buffer, HEPES 25 mM, 7.0 pH, containing CaCl$_2$ 75 mM. The obtained solution was allowed to recirculate through a 50 ml column loaded with a resin containing the immobilized enzyme.

This operation was performed at 28° C. with a flux of 200 ml/h for 24 hours.

The product obtained was purified by ultrafiltration and precipitated with ethanol. The precipitate was resolubilized in water at a concentration of 10%.

The obtained product shows an Epimerization percentage, measured with $^1$H-NMR, as iduronic acid percentage on the total uronic acids of 55% (as shown in picture 1).

d) Controlled Depolymerization.

The sample obtained in step c-2) underwent to controlled degradation with nitrous acid as described in patent WO 82/03627, In particular, 5 g of the sample were dissolved in 250 ml of water and taken to 4° C. with thermostated bath. The pH brought to pH 2.0 with 1 N hydrochloric acid cooled at 4° C. and, afterwards, 200 mg of sodium nitrite were added. When necessary the pH was brought to 2 with 1 N hydrochloric acid and kept under slow stirring for 15 minutes. The solution was neutralized with NaOH 1N cooled down at 4° C.

We added 250 mg of sodiumborohydride dissolved in 13 ml of deionized water leaving to react for 4 hours. The solution was taken to 5.0 pH with 1N chloride acid and left for 10 minutes to destroy the excess of sodium borohydride, and, afterwards, it was neutralized with NaOH 1N. The product was recovered through precipitation with 3 volumes of ethanol and, then, exsiccated in a vacuum stove. The obtained product shows a molecular weight of about 6,000 Da.

e) O-Partial Sulphation/O-Partial Desulphation

The product resulting from the previous step was re-suspended at a 10% concentration in water solution. The solution was cooled at 10° C. and allowed to flow at the temperature of 10° C., through a cationic exchange resin IR-120$^+$. After the flow of this solution, the resin was washed with deionized water, till the pH of the eluate was higher than 6. The acid solution was then led to neutrality by using a tertiary amine or a quaternary ammonium salt, such as for example tetrabutyl ammonium hydroxide in aqueous solution at 15%, obtaining as a result the ammonium salt. The solution was then concentrated at a minimum volume and lyophilized.

The resulting solution was resuspended into 100 ml of N,N-Dimethylacetamide (DMA) and pyridine —SO$_3$ was added.

Then a quantity of sulphating agent in a molar ratio between the sulphating agent and the epimerised K5 N-sulfate substrate (as hydroxyl moles) of 1.25 was added. The solution was kept at 50° C. for 360 minutes. At the end of the reaction the solution was cooled at room temperature and added with acetone saturated with sodium chloride till complete precipitation.

The precipitate was separated from the solvent by filtration, solubilized with a minimum quantity of deionized water and added with sodium chloride till a solution of 0.2 M was obtained. The solution was brought to pH 7.5 by addition of sodium hydroxide 2 N and acetone was added to allow precipitation. The precipitated solution was then separated from solvent through filtration. The solid solution thus obtained was solubilized by addition means of 100 ml deionised water and purified from residual salts by ultra filtration.

An aliquot was lyophilized for the structural analysis of the partially O-sulfated product by $^{13}$C-NMR.

The solution containing the partially sulfated product was allowed to flow through a cation exchange IR-120H$^+$ resin or equivalent. After the flow of this solution, the resin was washed with deionized water until the permeated pH was higher than 6. The acid solution was led to neutrality by adding pyridine. The solution was concentrated at a minimum volume and lyophilized. The product obtained was handled with 100 ml DMSO/methanol (9/1 V/V) solution and the obtained solution was kept at 65° C. for 240 minutes.

Finally, the solution was added with 200 ml deionised water and then handled with acetone sodium chloride saturation in such a quantity to complete the precipitation. The solid obtained was purified through diafiltration according to known techniques and an aliquot was lyophilized for structural analysis by $^{13}$C-NMR.

f) partial 6O-sulphation

The product obtained from step e) was then re-suspended into a water solution at a concentration of 10% and kept at room temperature. The solution was passed through a cationic exchange resin IR-120H$^+$. The resin was then washed with deionised water and led to neutrality by means of tetrabutylammonium hydroxide in aqueous solution, obtaining the ammonium salt. The solution was then concentrated in minimum volume and lyophilized.

The product obtained was then suspended into 100 ml of DMF and the sulphating agent pyridine-$SO_3$ added into a DMA solution was then added. The solution brought to 10° C. and treated with a quantity of as sulphating agent pyridine-$SO_3$ adduct with respect with 1.25 equivalents of sulphating agent in respect to hydroxyl for 60 minutes.

The solution was treated with acetone saturated with sodium chloride in a quantity to complete precipitation. The solid obtained was purified through diafiltration according to known method. An aliquot was lyophilized for the structural analysis by $^{13}$C-NMR.

g) N-resulphation

The product was solubilized in water, brought to a temperature of 40° C. and added by a single addition of 10 g sodium carbonate and 10 g-pyridine-sulphotrioxide in a time of 10 minutes.

At the end of the reaction, when necessary, the solution was led to room temperature, and then, if necessary, at pH lower than 8.0 with NaOH.

The product was then purified from salts by known techniques, such as for example by diafiltration with a 1,000 Da cut-off spiral membrane (prep-scale cartridge-Millipore). The process ended with a permeate conductivity lower than 1,000 μS, preferably lower than 100 μS. The retained product was reduced in volume till we obtained a 10% concentration of the polysaccharide by the same filtration process was achieved.

The spectrum $^1$H-NMR is shown in picture 2.

The anti-Xa activity measured into human plasma of the obtained products was 140 IU/mg (see table 2) and the ratio between the anti-Xa activity and the anti-II activity was 2.5.

Example 2

O-Sulphation with DMF

Figure 3:
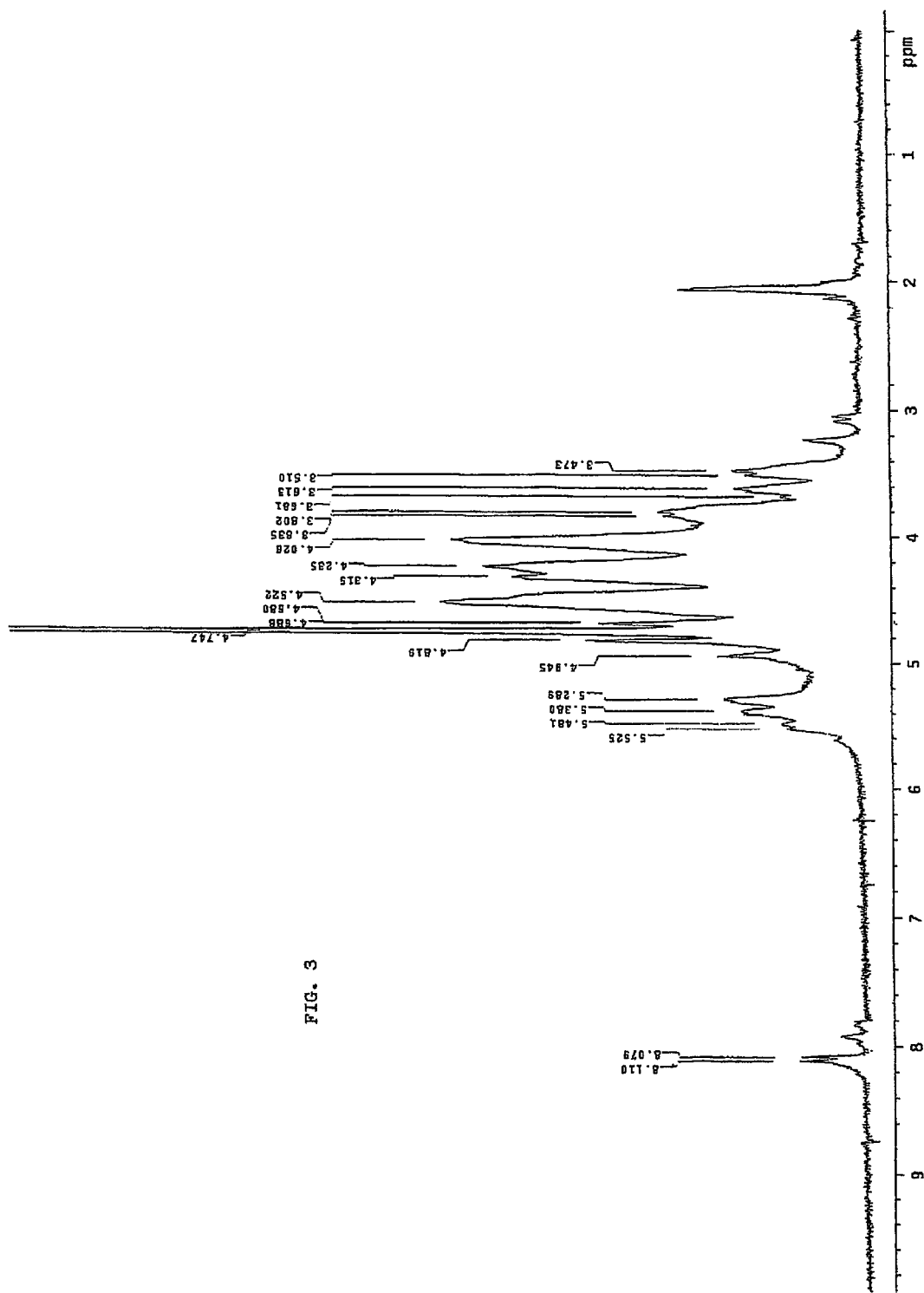
FIG. 3 spectrum $^1$H-NMR of the product obtained in example 2.

Example no. 1 was repeated with the variation that in step c) and f) the partial O-sulphation and partial 6O-sulphation were carried out using N,N-dimethylformamide (DMF) as organic solvent. The obtained product showed an anti-Xa activity in plasma of 85.9 IU/mg (see table 2). NMR spectrum is shown in FIG. 3.

Example 3

Controlled Depolymerization in Presence of 50 mg/g Substrate of Sodium Nitrite

Example no. 1 was repeated with the difference that the controlled depolymerization was performed with 50 mg sodium nitrite per g of polysaccharide in order to obtain a molecular weight of about 4,200 Da.

Figure 4:
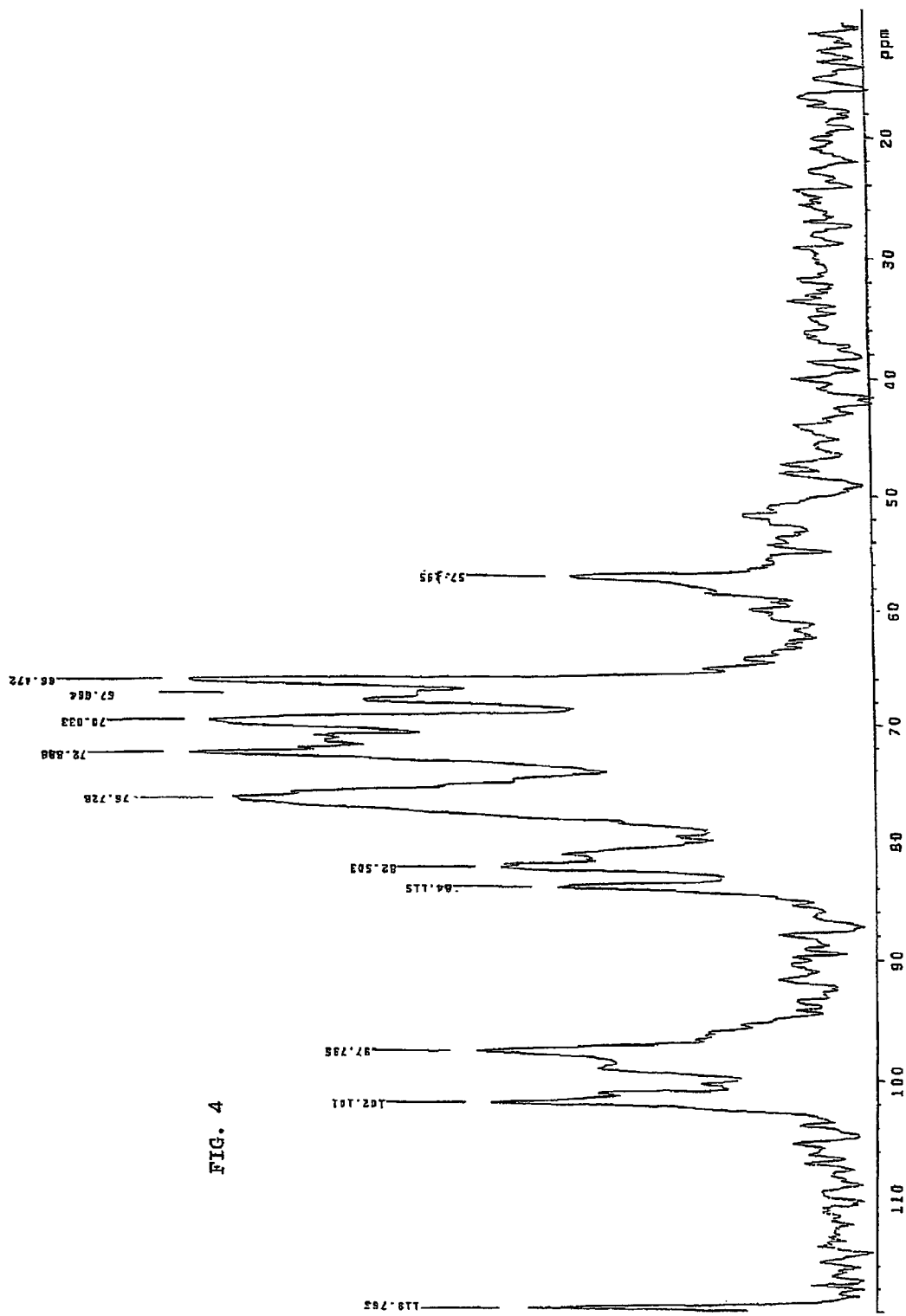
FIG. 4 spectrum $^{13}$C-NMR of the product obtained in example 3.

The product obtained showed an anti-Xa activity in plasma of 60.1 IU/mg (see table 2). The $^{13}$C-NMR spectrum is shown in FIG. 4.

Example 4

Production of Biotechnological Heparins Having a Molecular Weight of about 8,000 Da (Controlled Depolymerization with 20 mg/g Substrate of Sodium Nitrite)

Example no. 1 was repeated with the difference that in step d) the controlled depolymerization was carried out with 20 mg sodium nitrite per g of polysaccharide in order to obtain a molecular weight of about 8,000 Da.

Figure 5:
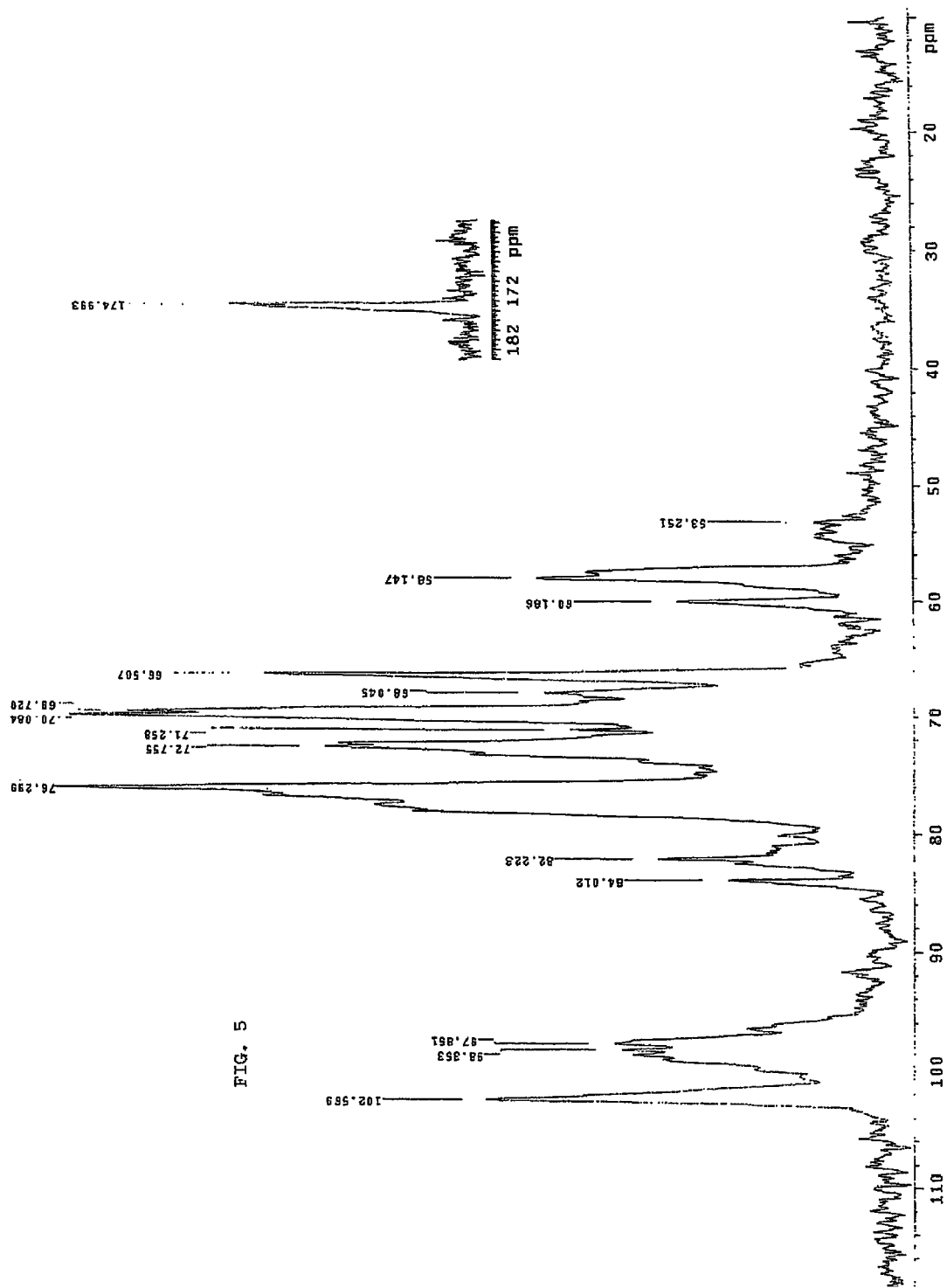
FIG. 5 spectrum $^{13}$C-NMR of the product obtained in example 4.

The obtained product showed an anti-Xa activity in plasma of 150 IU/mg (see table 2). The $^{13}$C-NMR spectrum is shown in FIG. 5.

Example 5

Biotechnological Heparins Production Having Molecular Weight of Around 20,000 Da Example no. 5 was performed according to the following steps a) preparation of N-acetyl heparosan polysaccharide starting from *Escherichia coli* K5;

b) N-deacetylation/N-sulphation;

c) epimerization;

d) partial O-Sulphation/partial O-desulphation;

e) partial 6O-sulphation/N-resulphation,

Steps a)-c) correspond to their respective steps in example 1, and where, lacking the depolymerization (step d), step d) corresponds to step e) in example 1 and step e) corresponds to step f) and g) in example 1.

The final product obtained had a molecular weight of about 20,000 Da, and is susceptible of depolymerization. The anti-Xa activity in plasma was 135 IU/mg (see table 2).

Figure 6:
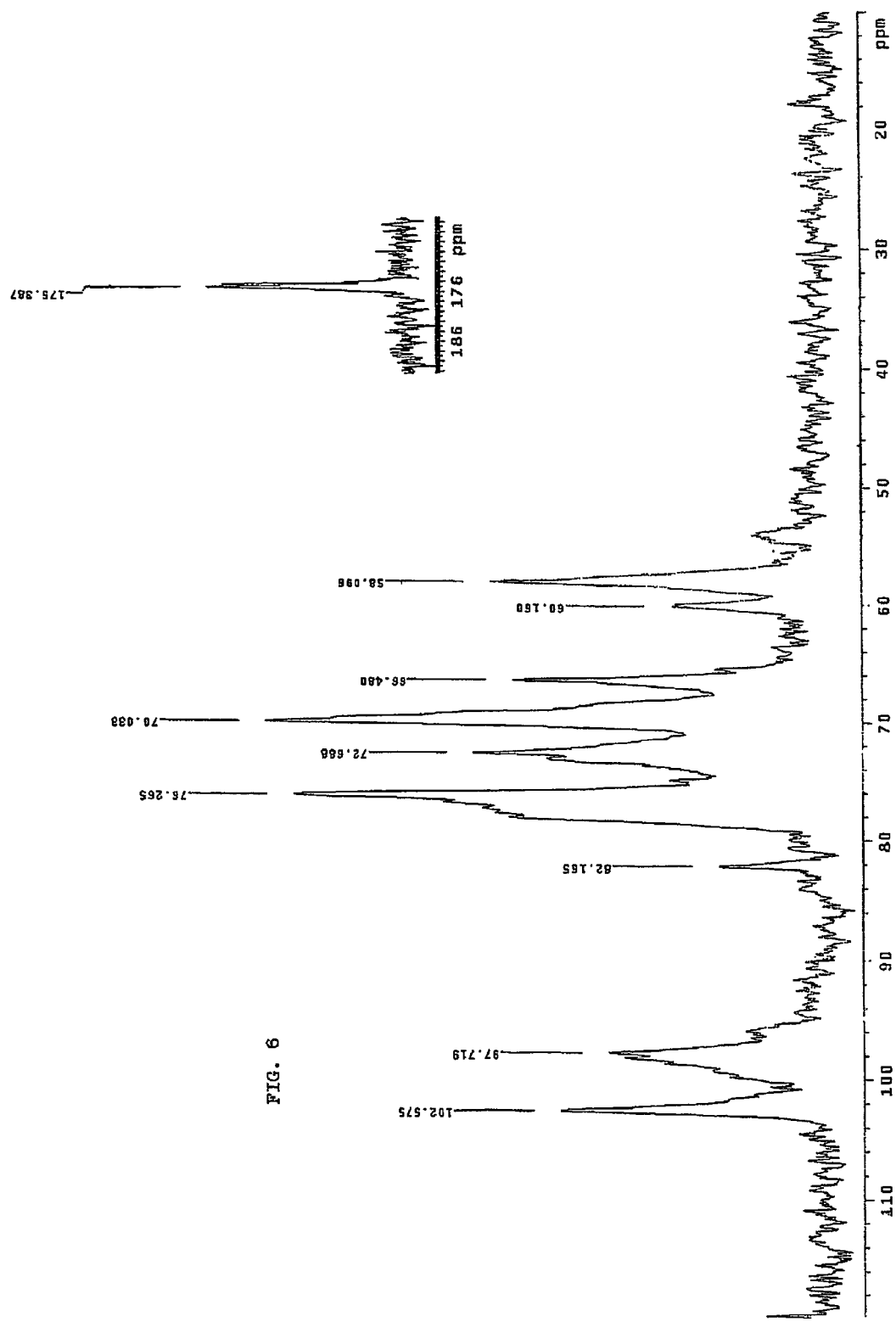
FIG. 6 spectrum $^{13}$C-NMR of the product obtained in example 5.

The $^{13}$C—NMR spectrum is shown in FIG. 6.

Example 6

Production of Biotechnological Heparins Production Having Molecular Weight of Around 15,000 Da (Controlled Depolymerization with 5 mg/g Substrate of Sodium Nitrite)

Example 1 was repeated under the same temperature and time conditions used in step d) but the controlled depolymerization with sodium nitrite was carried out with 5 mg of sodium nitrite per g of polysaccharide in order to obtain a molecular weight of about 15,000 Da.

Figure 7:
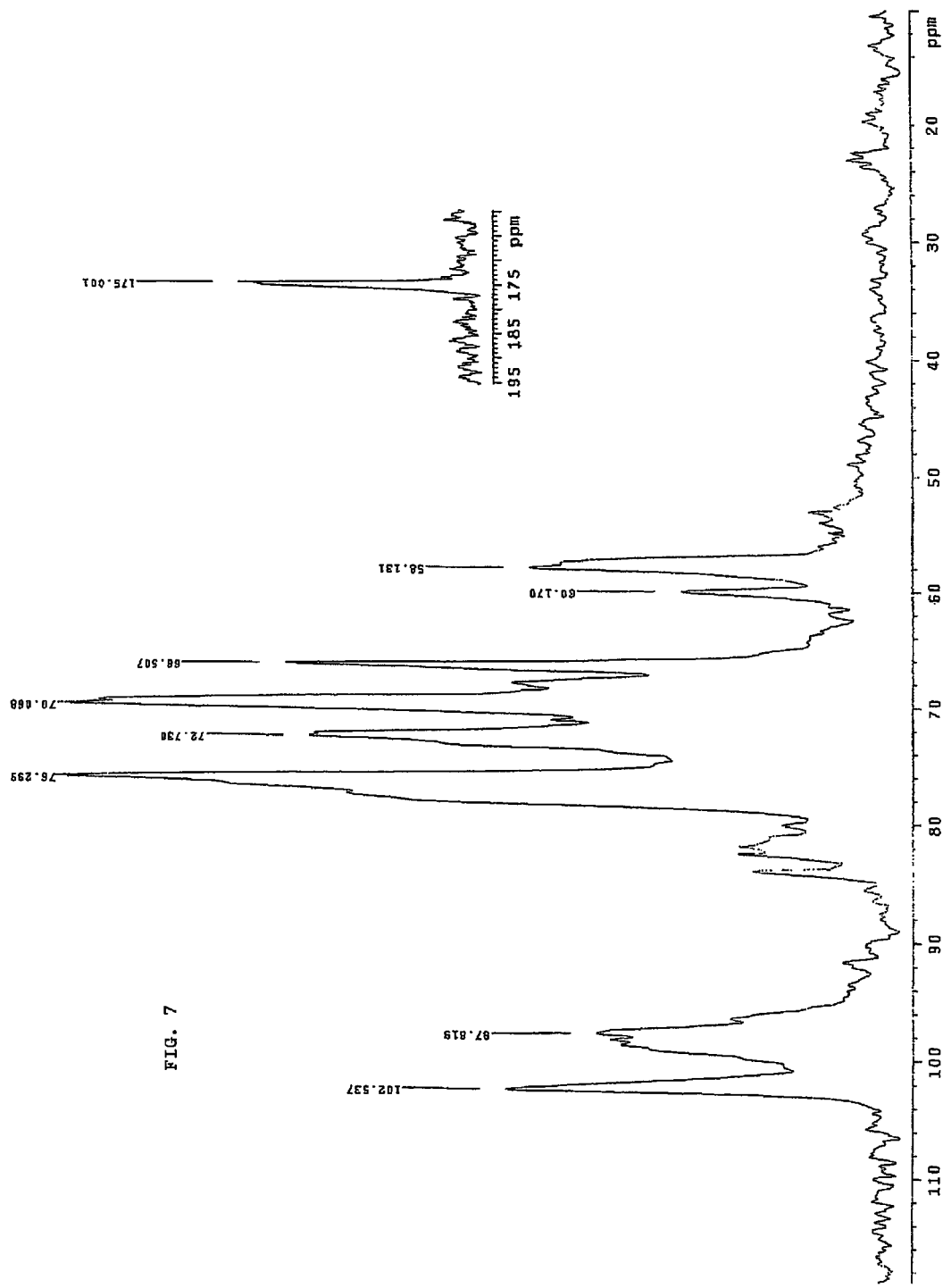
FIG. 7 spectrum $^{13}$C-NMR of the product obtained in example 6.

The obtained product showed an anti-Xa in plasma activity of 180 IU/mg (see table 2); the $^{13}$C-NMR spectrum is shown in FIG. 7.

Example 7

Process of Preparation of Biotechnological Heparin According to Known Techniques In this example the O-supersulphation and 6O-sulphation process conditions described in WO 01/72848 and WO 02/50125 were used. Briefly, performing the supersulphation in N,N-dimethylformamide at 50° C. for 18 hours, the O-desulphation at 65° C. for 150 minutes and the 6O-sulphation in N,N-dimethylformamide at 0° C. for 90 minutes.

Figure 8:
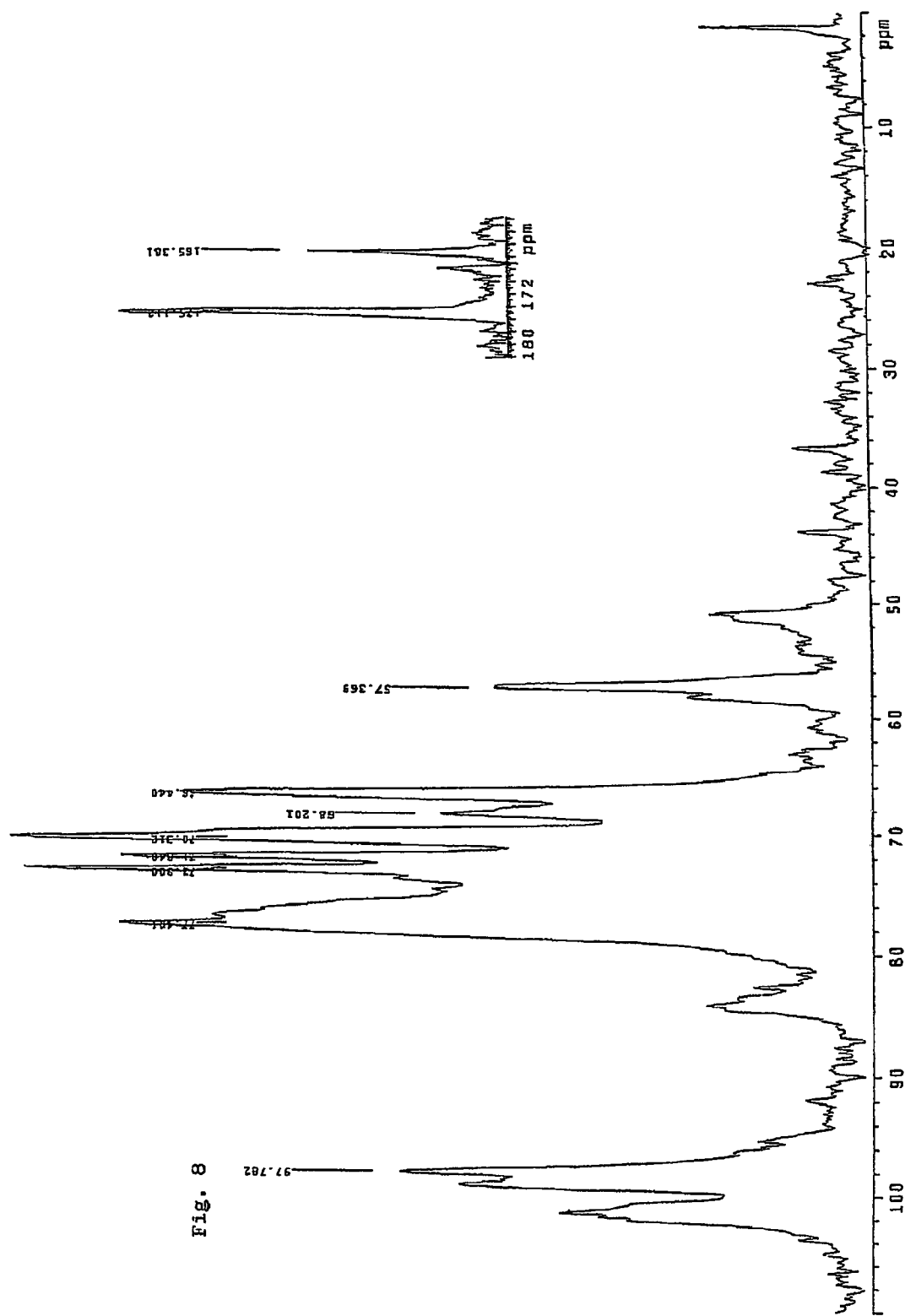
FIG. 8 spectrum $^{13}$C-NMR of the product obtained in example 7.

The final product showed a molecular weight of about 20,000 Da and an anti-Xa activity in plasma of 45 IU/mg (see table 2). The $^{13}$C-NMR spectrum is shown in FIG. 8.

Example 8

Production of Biotechnological Heparins According to Prior Art Techniques

This example was performed by using the same supersulphation and 6O-desulphation conditions described in WO 01/72848 and WO 02/50125: in brief, the supersulphation was performed in N,N-dimethylformamide at 50° C. for 18 hours, the O-desulphation at 65° C. for 150 minutes and the 6O-sulphation in N,N-dimethylformamide at 0° C. for 90 minutes.

Moreover, a depolymerization step was performed at the end of sulphation process as described in WO 01/72848 and WO 02/50125 in the presence of 40 mg/g substrate of sodium nitrite at 4° C. for 15 minutes.

The obtained final product has a molecular weight of about 6,000 Da and an anti-Xa activity in plasma of 31.5 IU/mg. The $^{13}$C-NMR spectrum is shown in FIG. 9.

Example 9

Production of Biotechnological Heparins: Control of Depolymerization and Sulphation Conditions Example 1 was repeated with the following variations The controlled depolymerization (step d) in example 1) was performed with 40 mg of sodium nitrite per g of epimerised K5NS under the same time and temperature conditions of example 1. The molecular weight obtained was about 6,500 Da.

Partial sulphation (step e) of example 1 was performed with a molar ratio of 5 between sulphating agent and substrate K5N-sulfated epimerised and for a period of 180 minutes, while O-desulphation was made for 60 minutes.

Figure 10:
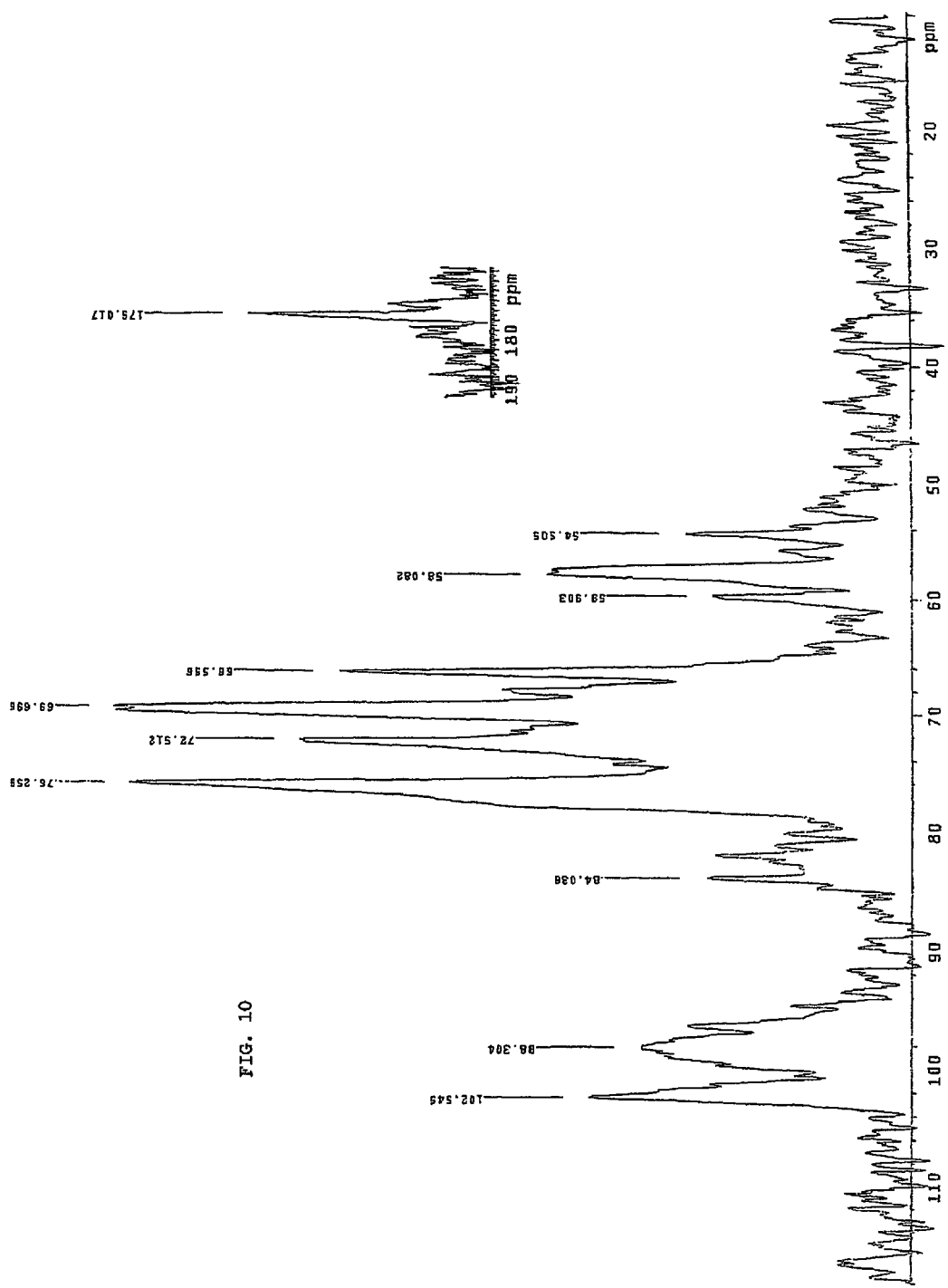
FIG. 10 spectrum $^{13}$C-NMR of the product obtained in example 9.

The product obtained showed an anti-Xa activity in plasma of 89 IU/mg (see table 2). The $^{13}$C-NMR spectrum is shown in FIG. 10.

Example 10

Production of Biotechnological Heparins: Control of the Depolymerization and Sulphation Conditions Example 1 was repeated and the intermediate depolymerization (step d) on K5 N-sulphated epimerised polysaccharide was performed under the same time and temperature conditions described in Example 9 but using 40 mg of sodium nitrite per mg of epimerised K5NS to obtain a molecular weight of about 6,500 Da. The partial sulphation corresponding to (step e) in example 1) was carried using molar ratio of 0.6 between sulphating agent and the epimerised substrate K5N-sulfated in a 8 hours incubation time. O-desulphation was carried out for 30 minutes.

The product obtained showed an anti-Xa activity in plasma of 101 IU/mg (see table 2).

$^{13}$C-NMR spectrum of the product obtained according to this example is shown in FIG. 11.

Example 11

Separation of Polysaccharide Fractions Having Great Affinity for Antithrombin III by Means of Selection on Affinity Column A polysaccharide was prepared according to Example 1. After step g) of N-resulphation the product was allowed to pass through an affinity column as follows:

20 mg of product obtained from step g) in example 1 were loaded on a CNBr sepharose 4B resin column (Pharmacia), on which were previously immobilized, according known techniques, 100 mg of human antithrombin III (Kedrion SpA, Lucca, Italia), in buffer Tris-HCl 10 mM at pH 7.4 and 0-0.15 M NaCl, at 4° C. After a period of 60 minutes of binding, the column was washed with at least 3 volumes of buffer Tris-HCl 10 mM pH 7.4.

The molecules bound with a greater affinity to the column were eluted by adding a gradient of Tris HCl 10 mM pH 7.4 containing 2M NaCl.

The eluted material was diafiltered by a 1,000 Da cut-off spiral membrane to eliminate the salts and concentrated by lyophilization.

The final product showed a molecular weight of 8,500 Da and an anti-Xa activity in plasma of 300 IU/mg 8 see table 2). $^{13}$C-NRM spectrum is shown in picture 12.

Example 12

Biotechnological Heparins Production Having Low Molecular Weight of about 6,000 Da Example 5 was repeated but after the N-resulfation step the product was depolymerised under the same conditions as described in step d) of example 1.

Figure 13:
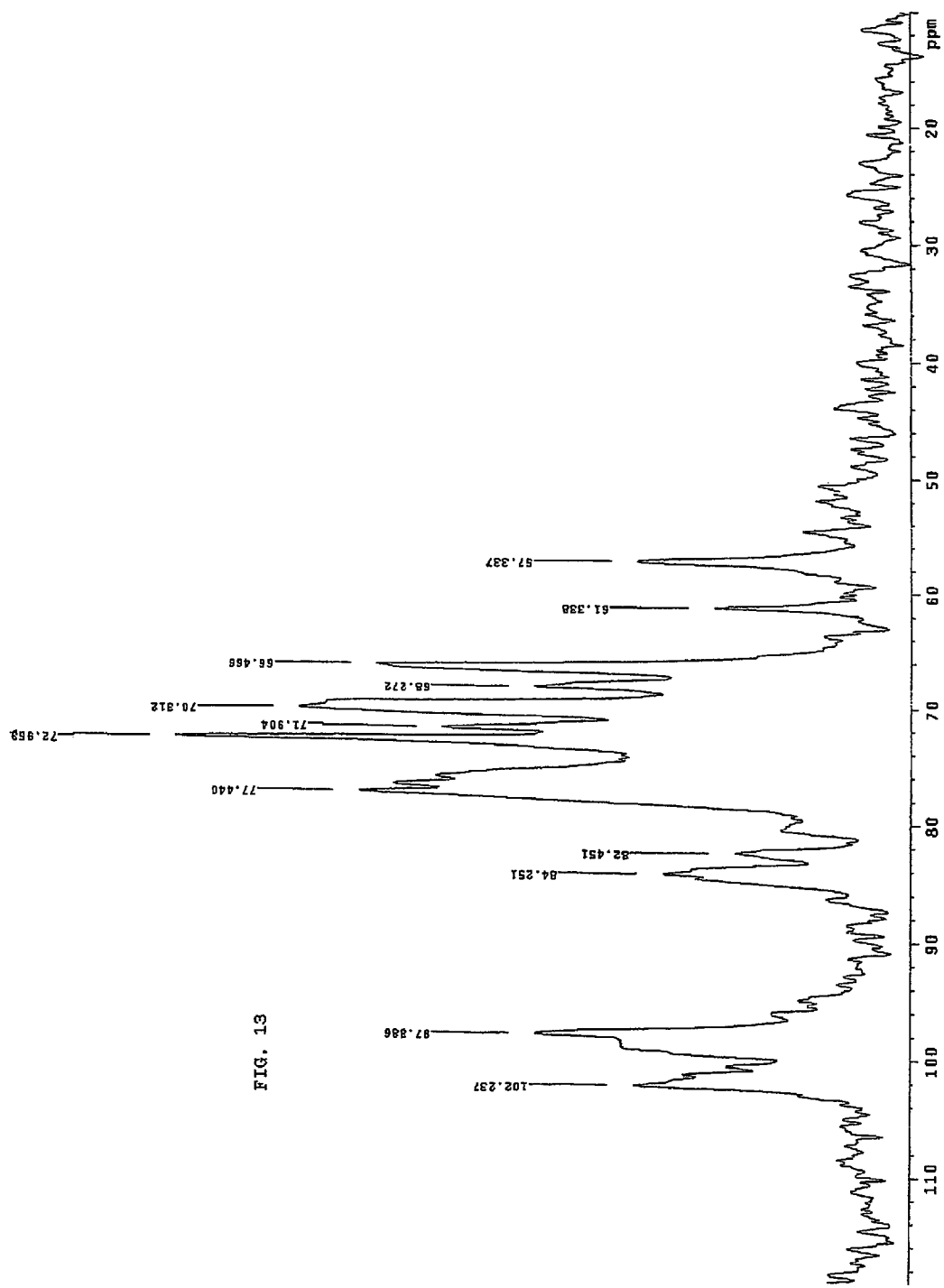
FIG. 13 spectrum $^{13}$C-NMR of the product obtained in example 12.

The final product obtained had a molecular weight of about 6,000 Da and an anti Xa activity in plasma of 65 IU/mg (see table 2). The $^{13}$C-NMR spectrum is shown in FIG. 13.

Example 13

Biotechnological Heparins Production: Control of the Sulphation Conditions

Example 1 was repeated varying the O-sulphation (step e) of Example 1, which was carried out with a molar ratio of 5 between the sulphating agent and the epimerised K5 N-sulphated substrate) for 8 hours at 50° C.

Figure 14:
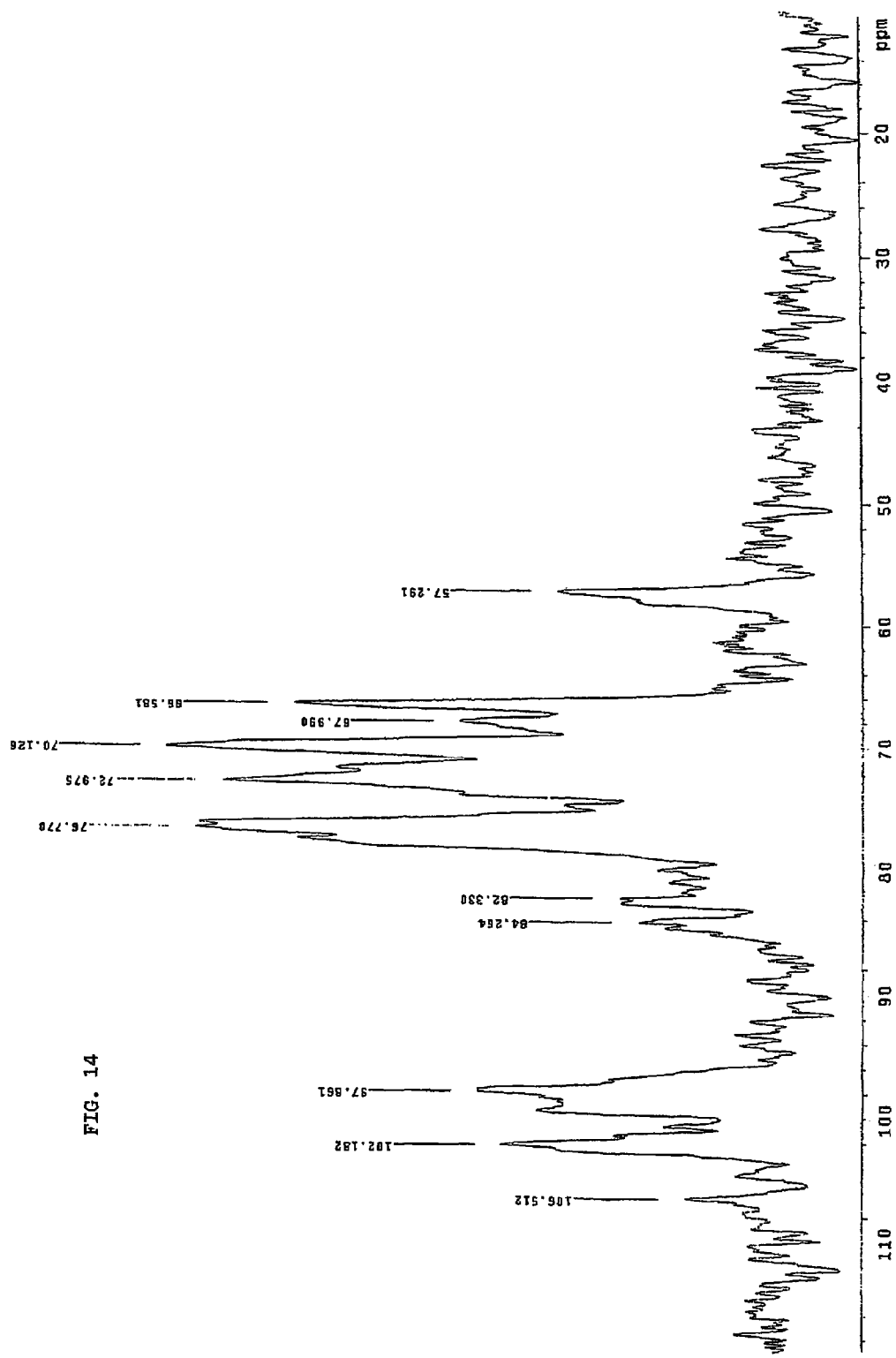
FIG. 14 spectrum $^{13}$C-NMR of the product obtained in example 13.

The product obtained showed an antiXa activity in plasma of 75 IU/mg. The $^{13}$C-NMR spectrum is shown in FIG. 14.

Example 14

Preparation of K5-OS6OSNH$_2$,Epi Intermediate (Non Re-Sulphated Intermediate of Biotechnological Heparin)

Example 1 was repeated without the last step of resulphation.

Figure 15:
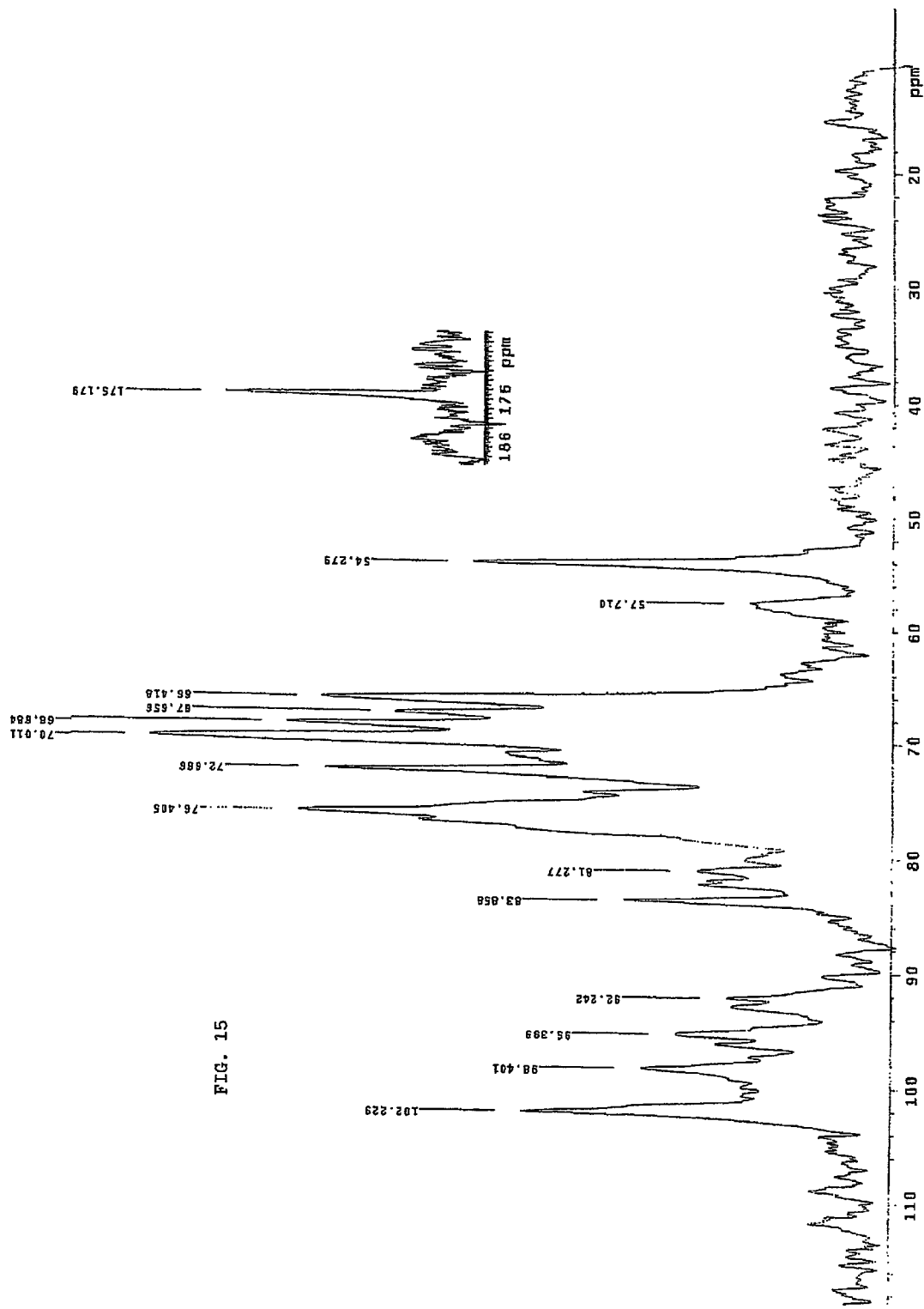
FIG. 15 spectrum $^{13}$C-NMR of the product obtained in example 14.

The final product had a molecular weight of about 6,000 Da and an anti Xa activity of 5 IU/mg (see table 2). The $^{13}$C-NMR spectrum is shown in FIG. 15.

Example 15

Preparation of K5-OS,NH$_2$,epi Intermediate (Intermediate of Biotechnological Heparin Before the Desulphation, 6O-Sulphation and N-Resulphation Steps)

Example 1 was repeated by varying the partial O-sulphation (step e) of Example 1) conditions, as it was carried out with a molar ratio of 5 between sulphating agent and the hydroxyls of the epimerised K5 N-sulphated substrate for 8 hours at 50° C. and without the subsequent steps of desulphation, partial 6O-sulphation and N-resulphation.

Figure 16:
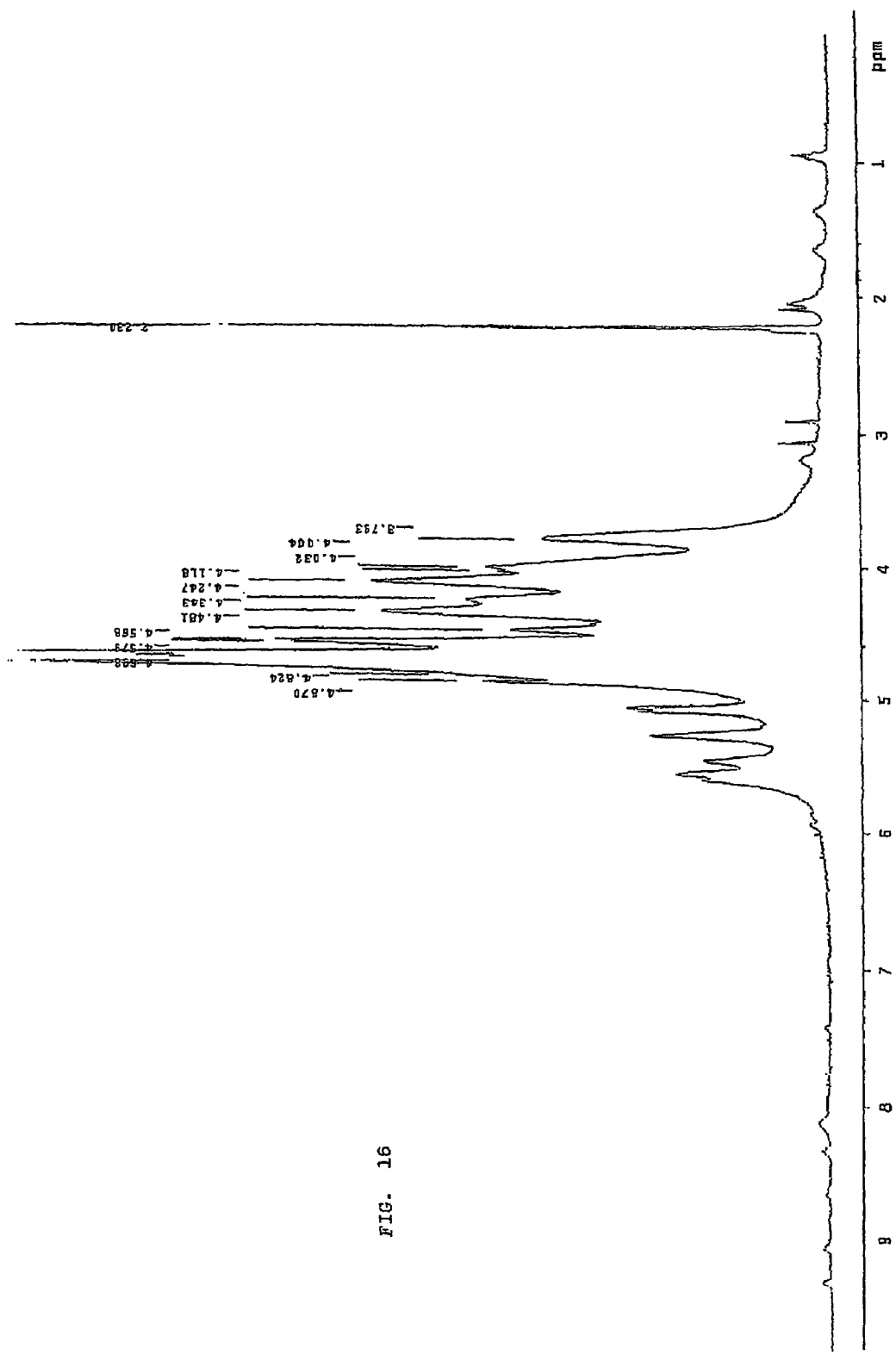
FIG. 16 spectrum $^{13}$C-NMR of the product obtained in example 15.
Figure 17:
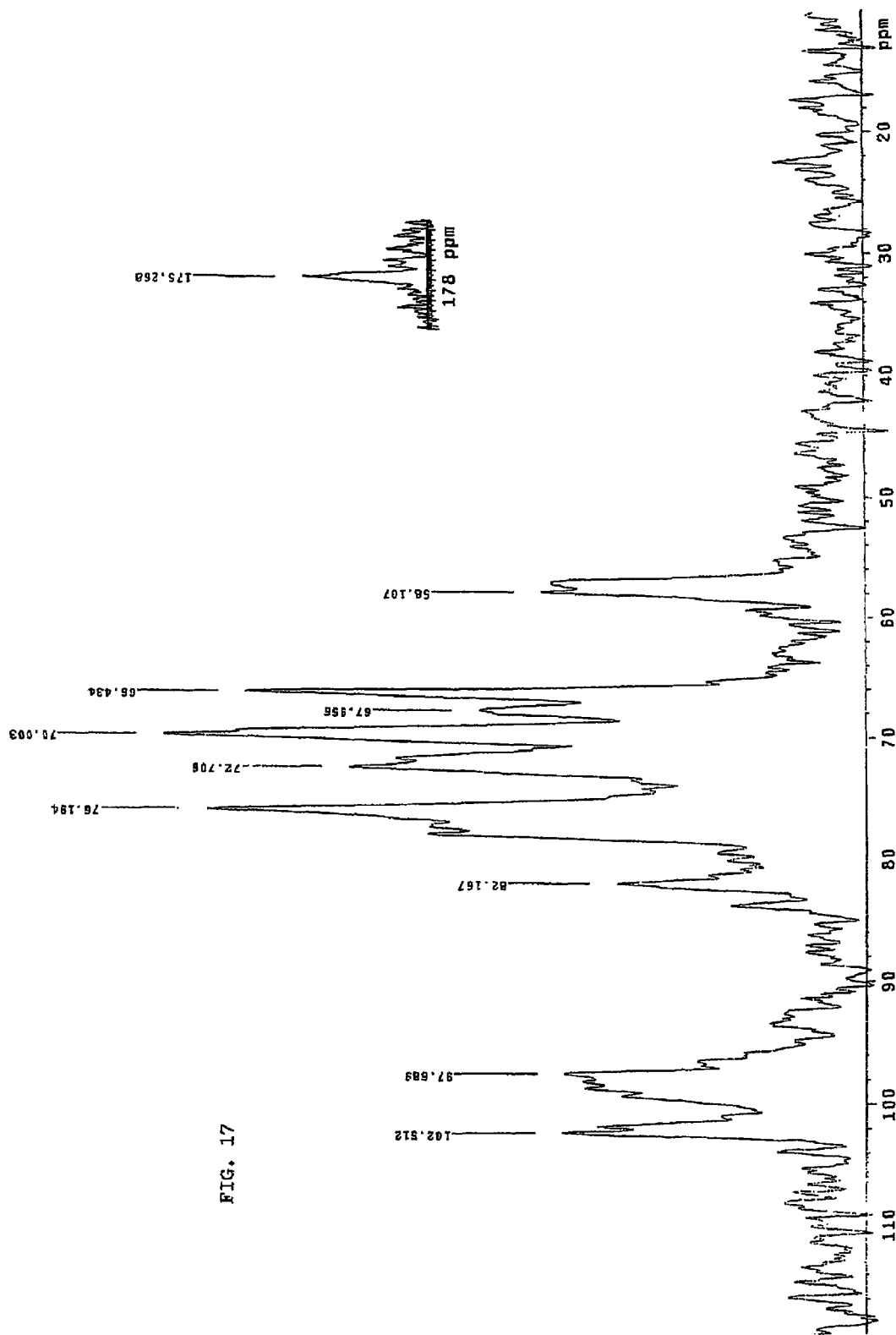
FIG. 17 spectrum $^{13}$C-NMR of the product obtained in example 16.

The obtained K5-OSNH$_2$-epi product had a molecular weight of about 6,000 Da, a 95% hydroxyls sulphation and an anti Xa activity of 8 IU/mg (see table 2). The proton $^1$H-NMR spectrum is shown in FIG. 16.

Example 16

Production of Biotechnological Heparins with Molecular Weight about 6,000 Da Example 1 was carried out with the following steps a) preparation of N-acetyl heparosan polysaccharide starting from K5 *Escherichia coli* b) N-deacetylation/N-sulphation c) epimerization d) partial O-sulphation/partial O-desulphation e) controlled depolymerization f) partial 6O-sulphation/N-resulphation, where the conditions of steps a)-c) correspond to those described in the respective steps of example 1 and where steps d) and e) are in an inverted order with respect to the same steps of example 1.

The obtained final product had a molecular weight of about 6,000 Da, and an anti Xa activity in plasma of 95 IU/mg (see table 2). The $^{13}$C-NMR spectrum is showed in picture 17.

Example 17

Determination of the Biological Activity of the Products Obtained According to Invention Measurement of the anti factor Xa activity: The anti factor-Xa activity was estimated according to a chromogenic method (Coatest Heparin kit, Chromogenix). The measure was performed in normal human plasma, using as reagents the chromogenic substrate S2222 (Chromogenix), Xa bovine factor (Chromogenix) and human Antithrombin III (Chromogenix). The reaction was performed at 37° C. in a coagulometer ACL 9000 (International Laboratory) and the reading was made at 405 nm. Results are shown in table 2. Results obtained according the known techniques (particularly products of the procedures made as described in WO 01/72848 and WO 02/50125) have been summarized in table 1, where data of the literature for extractive heparin have been reported (Fareed J et al. Exp Opin. Invest. Drugs, 1997, 6:705-733).

Anti-factor activity IIa. Anti-factor activity IIa was estimated in normal human plasma according to the following protocol:

30 µl of 0.5 U/ml of human antithrombin III (Chromogenix) were mixed to 30 µL of a solution of the sample to be investigated in different concentration and to 60 µl of bovine thrombin at 5.3 nKat/ml (Chromogenix).

The solution was incubated for 70 seconds at 37° C., then 60 µl of chromogenic substrate S-2238 (Chromogenix) were added. The reaction was recorded for 90 seconds with a reading every second at 405 nm using a coagulometer ACL 9000 (International Laboratory). The results obtained with the known products (mainly products of the process described in WO 01/72848 and WO 02/50125) have been summarized in table 1.

Resistance to heparinase. The resistance to heparinase I was estimated by preparing low and high molecular weight samples, in buffer Tris HCl 20 mM, 50 mM NaCl, 4 mM CaCl$_2$ and 0.01% BSA at pH 7.5 at a final concentration of 0.02%. 20 units of heparinase I (Sigma, CAS number 52227-76-6) were added to a 100 µl solution containing the sample and the reaction was incubated at 25° C. The reaction was then stopped by addition of HCl 50 mM, at regular intervals every 10 min, 1 hour, 2 hours, 20 hours.

Every sample was analyzed both by spectrophotometrical determination at 235 nm and by GPC-HPLC to determine the molecular weight. The results obtained are shown in table 3, where it can be observed that while extractive heparins used in the study both high (HMW) and low molecular weight (Fraxiparina, Sanofi) have been degraded in the long run as shown by the decrease in the molecular weight, biotechnological heparins obtained according to this invention are stable (molecular weight is stable even after 20 hours treatment with heparinase I).

TFPI activity. The determination of the activity on the basis of TFPI factor was made in vitro on HUVEC cells according to the method described in Gori A M. et al. Thromb. Haemostasis 1999:81:589-93 and the comparison was made with a commercial non-separated heparin (table 4).

Inhibition of proteases generation. The determination of inhibition of the proteases generation was performed in plasma depleted of fibrinogen according to the method reported in Fareed et al. Path. Haem. Thromb. 2002; 32 (3): 56-65. After adding various dilutions of the samples under examination, plasma was activated by adding PT (thromboplastin C) for the activation of the intrinsic coagulation system or APTT (Dade Actin) for the activation of the intrinsic coagulation system.

The inhibition of both thrombin (factor II) and of Xa factor was monitored using a ACL 9000 coagulometer (International Laboratory). The values obtained with a sample dilution of 50 µg/ml are shown in table 5.

Affinity to factor PF4: determination of the affinity to factor PF4 (platelet factor 4) was evaluated in plasma by determining the residual anti Xa activity after addition of a fixed quantity of PF4 factor in the solution containing the biotechnological heparins obtained according to the invention.

100 µg plasma containing 0.8 anti Xa IU/ml were added obtaining a PF4 final concentration of 10 µg/ml. The residual anti Xa activity of the sample was measured using a Coatest heparin kit (chromogenix) by the coagulometer ACL 9000 (International Laboratory). The residual anti Xa activity was measured as percent of the initial activity (table 6).

Measurement of activated partial thromboplastin time (APTT): the determination of APTT was performed by coagulation test using a coagulometer ACL 9000 (International Laboratory). The reaction was carried out at 37° C. by adding a quantity of cephalin (kit APTT International Laboratory cod 8468710) to the sample duly diluted and following the clot formation after calcium chloride addition and reading the out put at 660 nm.

The APTT values are reported in table 2 as percent of activity with respect to the first international standard of low molecular weight heparin 85/600.

Determination of the activity of heparin cofactor II (HCII): the determination of HCII was carried out by preparing a reaction mixture containing 20 µl HCII (Stago) 0.085 PEU/ml, 80 µl solution of the sample under examination at different concentration, 50 µl of thrombin 0.18 U/ml (Boehringer) in 0.02 M tris-buffer, pH 7.4, 0.15 M NaCl and 0.1% of PEG 6000. The solution was incubated for 60 seconds at 37° C., then, 50 µl of 1 mM of Spectrozyme chromogenic substrate (American Diagnostic) were added. The reaction was monitored for 180 seconds at 1 second intervals at 405 nm wavelength on an automatic coagulometer ACL 9000 (instrumentation Laboratory).

HCII values are reported in table 2 as percent of activity with respect to the first international standard of low molecular weight heparin 85/600.

In table 1 and 2 the biological activity data of biotechnological heparins produced according to the invention, or according to methods characterized by O-supersulfation regardless the use of solvents donor or non-donor of formyl groups such as N,N-dimethylformamide and by a final depolymerization step, or of extractive heparins. The data show in particular that the anti-Xa activity measured in human plasma is higher for the products obtained according to this process than for the prior art products at comparable molecular weight.

In fact in products obtained according to the invention the ratio between biological activity expressed as anti factor X activity and the molecular weight is higher. Such an increase seems to be due to the combined peculiarities of the process:

- O-sulphations (O-sulphation and 6O-sulphation) performed in mild conditions (see examples 5 and 7 for a comparison);
- use of an aprotic polar solvent non-donor of formyl groups during the O-sulphation and the 6O-sulphation steps (see examples 1 and 2 for a comparison);
- intermediate depolymerization step, which is performed before the O-sulphation or before the 6O-sulphation steps, compared to depolymerization carried out at the end of the process (see examples 1 and 12 for a comparison).

A higher increase of the ratio between the biological activity, considered as the anti Xa activity in plasma and the molecular weight of the product obtained, as well as of the ratio between the anti Xa and anti IIa activity is obtained when the O-sulphations (O-sulphation and 6O-sulphation) are partial together with the use of a polar aprotic solvent non-donor of formyl groups for O-sulphation and 6O-sulphation coupled to depolymerization performed in an intermediate phase as in example 1 and in example 6.

However, the process is compatible also with a stronger O-sulphation combined with partial 6O-sulphation, as described in example 13.

Moreover, the process of the invention is also compatible with a final depolymerization as described in example 12.

An additional parameter improved in the products of the invention, as compared to biotechnological heparins obtained according to known method, is the ratio between anti-Xa activity and anti IIa activity indicating a relation between antithrombotic and anticoagulant characteristics, resulting also from APTT values which is similar to value of extractive heparins.

In the products obtained according to the invention such ratio is equal to or higher than 1, while is lower than 1 in products obtained according to prior art processes. Another characteristic shown by the high HCII values, is a greater ability to inhibit directly thrombin, as compared to extractive heparins.

Example 18

Production of Biotechnological Heparins with Molecular Weight about 6,000 Da.

Example 1 was carried out according to the following steps a) preparation of N-acetyl heparosan polysaccharide starting from K5 *Escherichia coli* b) N-deacetylation/N-sulphation c) epimerization d) partial O-sulphation/partial O-desulphation e) N-resulphation f) controlled depolymerization g) partial 6O-sulphation where the conditions of steps a)-c) correspond to those described in the respective steps of example 1 and where steps but the d)-g) which are in an inverted order with respect to the same steps of example 1.

Figure 18:
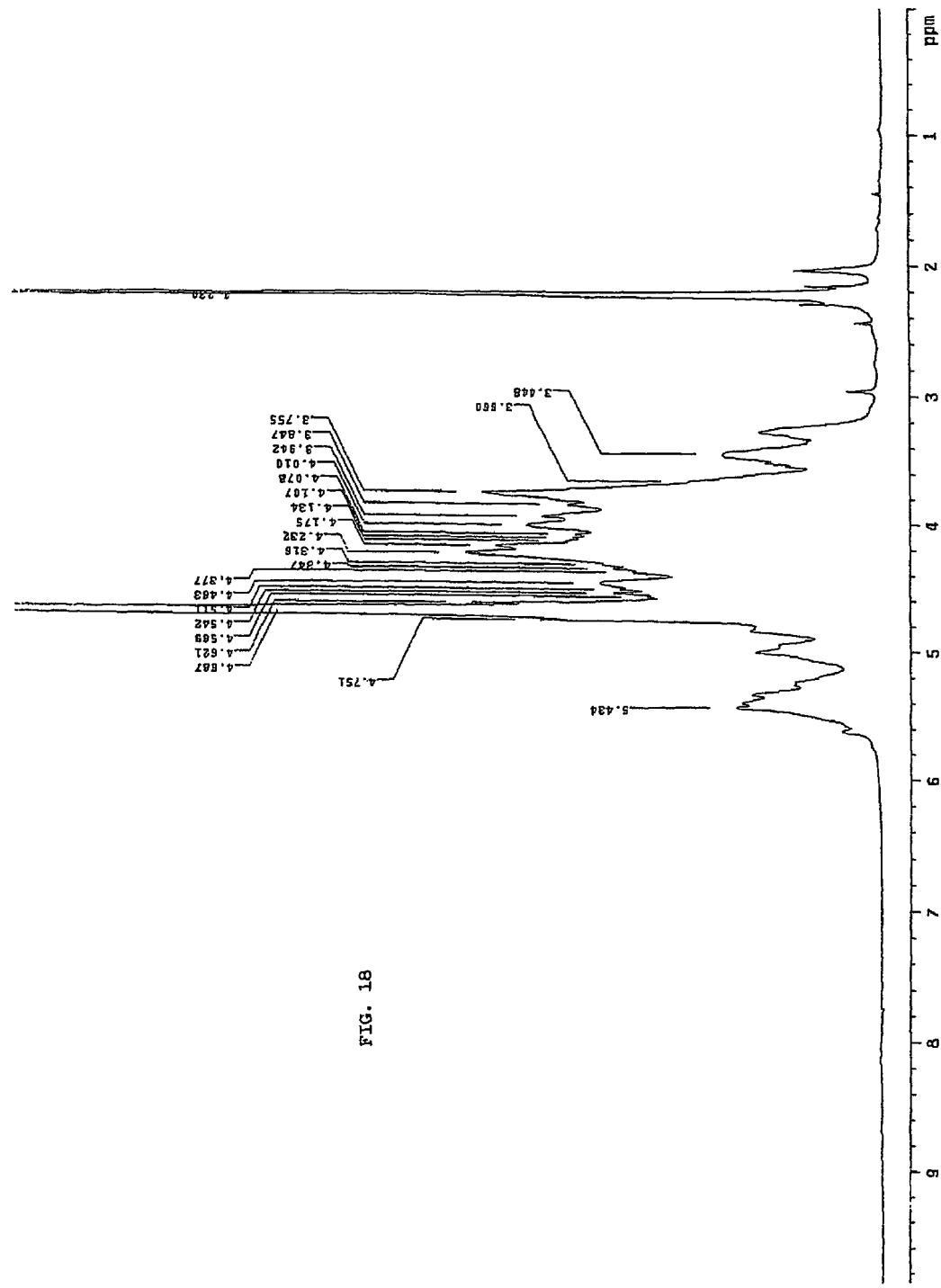
FIG. 18 spectrum $^1$H-NMR of the product obtained in example 18.

The obtained final product had a molecular weight of about 6,000 Da, and an anti Xa activity in plasma of 92 IU/mg (see table 2). The proton NMR spectrum is showed in FIG. 18.

TABLE 1

Comparative table of biological activity data.

| Product | O-sulphation and depolymerization | Molecular weight range (Da) | AntiXa activity in human plasma | Anti IIa activity in human plasma | anti Xa/MW(KDa) ratio | antiXa/anti IIa ratio |
|---|---|---|---|---|---|---|
| Unfractionated extractive heparin (UFH) | — | 11,000-15,000 | 160-200* | 160-200* | 13-14 | 1.0 |
| Extractive heparin LMW | — | 3,900-6,700 | 80-150* | 25-60* | 15-25 | 1.8-4.0 |
| Product Ex. n° 7, WO 01/72848, | Supersulphation | 20,000-30,000 | 30-80 | 70-80 | 1.5-3 | 0.5-0.8 |
| Product Ex. n° 8, WO 01/72848, | Supersulphation Final depolymerization | 4,000-8,000 | 15-50 | 40-70 | 3-6 | 0.5-0.8 |
| Product Ex. n° 6 | Partial O-sulphation Partial 6O-sulphation Intermediate depolymerization | 9,000-15,000 | 150-190 | 100-150 | 10-12 | 1.0-1.5 |
| Product Ex. n° 1 | Partial O-sulphation Partial 6O-sulphation Intermediate depolymerization | 3,000-9,000 | 50-150 | 30-100 | 16-25 | ≧1.5 |
| Product Ex. n° 11 | Partial O-sulphation Partial 6O-sulphation Intermediate depolymerization Affinity column | 4,000-9,000 | 100-350 | 50-100 | 25-40 | ≧1.5 |

*values published in: Fareed et al. Exp. Opin. Invest. Drugs (1997) 6: 705-733, Eriksson B. et al. Tromb. Haemost. (1995) 73: 398

TABLE 2

Summary table: examples and biological activity of the products according to the invention.

| Ex. n° | Figure n° | MW (Da) HPLC | O-Sulphation | desulphation | Anti Xa in plasma (IU/mg) | antiXa/anti IIa | aPTT | HCII | notes |
|---|---|---|---|---|---|---|---|---|---|
| 1 | 1.2 | 6,000 | r.m = 1.25<br>6 hrs, 50° C. | 240 min<br>65° C. | 140 | 2.5 | 93 | n.d | see example 1 |
| 2 | 3 | 6,000 | r.m = 1.25<br>6 hrs, 50° C. | 240 min<br>65° C. | 85.9 | 1.5 | 84 | 364 | As in example 1 but with DMF |
| 3 | 4 | 4,200 | r.m = 1.25<br>6 hrs, 50° C. | 240 min<br>65° C. | 60.1 | 3.0 | 58 | 254 | As in example 1 with depolymerization to 4200 Da |
| 4 | 5 | 8,000 | r.m = 1.25<br>6 hrs, 50° C. | 240 min<br>65° C. | 150 | 2.0 | 98 | n.d | As in example 1 with depolymerization to 8000 Da |
| 5 | 6 | 20,000 | r.m = 1.25<br>6 hrs, 50° C. | 240 min<br>65° C. | 135 | 1.0 | n.d | 725 | As in example 1 without depolymerization |
| 6 | 7 | 15,000 | r.m = 1.25<br>6 hrs, 50° C. | 240 min<br>65° C. | 180 | 1.2 | n.a | n.a | As in example 1 with depolymerization to 15000 Da |
| 7 | 8 | 20,000 | Supersolf<br>18 hrs, 50° C. | 150 min<br>65° C. | 45 | 0.6 | n.d | n.d | Supersulphation and 6O-sulphation as in WO 01/72848 without depolymerization |
| 8 | 9 | 6,000 | Supersolf<br>18 hrs, 50° C. | 150 min<br>65° C. | 31.5 | 0.8 | n.d | n.d | Supersulphation and 6O-sulphation as in WO 01/72848 with final depolymerization |
| 9 | 10 | 6,500 | r.m = 5<br>3 hrs, 50° C. | 60 min<br>65° C. | 89 | 2.5 | 73.9 | 395 | As in example 1, with differences in step e) |
| 10 | 11 | 6,500 | r.m = 0.6<br>8 hrs, 50° C. | 30 min<br>65° C. | 101 | 2.5 | n.d | 423 | As in example 1, with differences in step e) |
| 11 | 12 | 8,500 | r.m = 1.25<br>6 hrs, 50° C. | 240 min<br>65° C. | 300 | 1.8 | 94.2 | n.d | As in example 1, with affinity column |
| 12 | 13 | 6,000 | r.m = 1.25<br>6 hrs, 50° C. | 240 min<br>65° C. | 65 | 1.0 | n.d | n.d | As in example 1, with final depolymerization |
| 13 | 14 | 6,000 | r.m = 5<br>8 hrs, 50° C. | 240 min<br>65° C. | 75 | 1.2 | n.d | n.d | As in example 1, with differences in step e) |
| 14 | 15 | 6,000 | r.m = 1.25<br>6 hrs, 50° C. | 240 min<br>65° C. | 5 | n.d | n.d | n.d | As in example 1, without N-resulphation |
| 15 | 16 | 6,000 | r.m = 5<br>8 hrs, 50° C. | 240 min<br>65° C. | 8 | n.d | n.d | n.d | As in example 13 without desulphation/6O-sulphation/N-resulphation |
| 16 | 17 | 6,000 | r.m = 1.25<br>6 hrs, 50° C. | 240 min<br>65° C. | 95 | 2.5 | n.d | n.d | As in example 1 with inversion of steps d) and e) |
| 18 | 18 | 6,000 | r.m = 1.25<br>6 hrs, 50° C. | 240 min<br>65° C. | 92 | 2.5 | n.d | n.d | As in example 1 with inversion of steps d)-g) | n.d. = not determined
r.m = molar ratio between the sulphating agent and substrate

TABLE 3

Comparative test of Heparinase hydrolysis of biotechnological and extractive heparins

| Sample | Time: 0 | Time: 10' | Time: 1 hour | Time: 2 hours | Time: 20 hours |
|---|---|---|---|---|---|
| Extractive heparin HMW (13,600 Da) | 12,788 Da | 8,930 Da | 4,191 Da | 5,007 Da | 4,082 Da |
| Extractive heparin LMW (Fraxiparina) | 5,718 Da | 4,602 Da | nd | 4,187 Da | 3,417 Da |
| Biotechnological heparin MW = 8,500 Da (Ex. n° 10) | 8,546 Da | 7,636 Da | 7,932 Da | 8,453 Da | 7,868 Da |
| Biotechnological heparin MW = 10,000 Da (Ex. n° 10 + depolym. to 10,000 Da) | 10,087 Da | 9,979 Da | 10,978 Da | 9,993 Da | 10,479 da |

TABLE 4

Release assay of TFPI factor from HUVEC cells in vitro

| Sample | TFPI released in medium (ng/ml) |
|---|---|
| Control (only culture medium) | 0.5-0.8 |
| Unfractionated extractive heparin (Vister, Pfizer) (1 IUaXa/ml) | 2.4-2.6 |
| Biotechnological heparin 6,000 Da (ex. n° 1) (1 IUaXa/ml) | 2.5-3.7 |
| Biotechnological heparin 8,500 Da (ex. n° 10) (1 IUaXa/ml) | 3.0-4.7 |

TABLE 5 inhibition assay of protease generation (thrombin and Xa factor).

| Sample | % Inhibition of Xa factor production | | % Inhibition of thrombin production | |
|---|---|---|---|---|
| | intrinsic | extrinsic | intrinsic | extrinsic |
| Extractive LMWH heparin | 50 | 90 | 0 | 0 |
| Biotechnological heparin 6,000 Da (ex. n° 1) | 80 | 90 | 65 | 80 |

TABLE 6 affinity assay for PF4 factor

| Sample | % residual Xa activity in PF4 presence |
|---|---|
| Unfractionated extractive heparin (UFH) | 45 |
| Low molecular weight extractive heparin (LMWH) | 65 |
| Biotechnological heparin 4,200 Da (ex. n° 3) | 90 |
| Biotechnological heparin 8,500 Da (ex. n° 10) | 70 |

The invention claimed is:

1. A process for the preparation of a glycosaminoglycan-sulphate having a ratio between factor Xa and factor IIa inhibition activities equal to or higher than 1.0, having a reduced hemorragic risk, and prepared from an *E. coli* K5 polysaccharide, the process consisting essentially of the following steps:
    (a) N-deacetylating and N-sulphating said *E. coli* K5 polysaccharide isolated from a natural or recombinant bacterial K5 strain;
    (b) enzymatically epimerizing and depolymerizing the N-deacetylated and N-sulphated polysaccharide, wherein said epimerizing comprises epimerizing with a glucuronyl C5-epimerase enzyme;
    (c) partially O-sulphating with a sulphating agent and partially O-desulphating the epimerized and depolymerized polysaccharide;
    (d) partially 6O-sulphating the polysaccharide obtained from step (c) with a sulphating agent; and
    (e) N-resulphating the 6O-sulphated polysaccharide, thereby providing the glycosaminoglycan-sulphate,
wherein in step (c), the partial O-sulphating is performed for a time equal to or less than 6 hours and the molar ratio between the sulphating agent and the epimerized and depolymerized polysaccharide *E. coli* K5 polysaccharide is equal to or less than 2.5; and wherein in step (d), the partial 6O-sulphating is performed for a time equal to or less than 2 hours and the molar ratio between the sulphating agent and the hydroxyl groups of the polysaccharide obtained from step (c) is less than or equal to 1.5.

2. The process of claim 1, wherein the partial 6O-sulphating of step (d) is performed at a temperature from 10° C. to 25° C.

3. The process of claim 2, wherein the partial 6O-sulphating of step (d) of the process is performed for a time equal to or less than 60 minutes.

4. The process of claim 3, wherein the 6O-sulphating of step (d) is carried out for a time equal to or less than 30 minutes.

5. The process of claim 1, further comprising (f) affinity selecting the glycosaminoglycan-sulphate on a matrix of antithrombin III.

6. The process of claim 1, wherein the partial O-sulphating of step (c) and the partial 6O-sulphating of step (d) are carried out in an aprotic solvent and with a sulphating agent selected from the group consisting of triethylamine-$SO_3$, trimethylamine-$SO_3$, and pyridine-$SO_3$.

7. The process of claim 6, wherein said aprotic solvent is polar, is not a donor of formyl groups, and is selected from the group consisting of tetramethylensolfone, 2,4-dimethylsulfolane, N,N-dimethylacetamide (DMA) and N,N,-diethylacetamide (DEA).

8. The process of claim 7, wherein the aprotic polar solvent is DMA and the sulphating agent is pyridine-$SO_3$.

9. The process of claim 1, wherein the depolymerizing of step (b) comprises chemically or physically depolymerizing the N-deacetylated and N-sulphated polysaccharide.

10. The process of claim 9, wherein physically depolymerizing comprises treating the epimerized polysaccharide with a gamma ray and wherein said chemically depolymerizing comprises treating the epimerized polysaccharide with nitrous acid or a salt thereof, a beta-elimination agent, a periodic acid, or a free radical.

11. The process of claim 10, wherein the depolymerizing comprises treating the epimerized polysaccharide with nitrous acid or a salt thereof.

12. The process of claim 11, wherein the nitrous acid or salt thereof and the epimerized polysaccharide are present in a ratio of milligrams nitrous acid or salt thereof to grams epimerized polysaccharide from 1:1 to 100:1 and wherein the depolymerizing is performed at a temperature from 4° C. to 10° C.

13. The process of claim 12, wherein the depolymerizing by treating with nitrous acid or a salt thereof comprises treating with nitrous acid or a salt thereof for less than 30 minutes.

14. The process of claim 13, wherein the nitrous acid salt is sodium nitrite.

15. The process of claim 11, further comprising stopping the depolymerizing by adding a molar excess of borohydride to the polysaccharide treated with nitrous acid or salt thereof.

* * * * *